US008318161B2

(12) United States Patent
Esue

(10) Patent No.: US 8,318,161 B2
(45) Date of Patent: Nov. 27, 2012

(54) ANTI-OXIDIZED LDL ANTIBODY FORMULATION

(75) Inventor: Osigwe Esue, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 140 days.

(21) Appl. No.: 12/718,783

(22) Filed: Mar. 5, 2010

(65) Prior Publication Data

US 2010/0239567 A1 Sep. 23, 2010

Related U.S. Application Data

(60) Provisional application No. 61/158,331, filed on Mar. 6, 2009.

(51) Int. Cl.
*A61K 39/395* (2006.01)
*A61K 39/00* (2006.01)

(52) U.S. Cl. .............. 424/130.1; 424/139.1; 424/133.1; 514/7.4

(58) Field of Classification Search .................. None
See application file for complete search history.

(56) References Cited

U.S. PATENT DOCUMENTS

| | | | |
|---|---|---|---|
| 4,075,193 A | 2/1978 | Campbell et al. | |
| 4,093,606 A | 6/1978 | Coval | |
| 4,374,763 A | 2/1983 | Takagi | |
| 4,499,073 A | 2/1985 | Tenold | |
| 4,877,608 A | 10/1989 | Lee et al. | |
| 4,940,782 A | 7/1990 | Rup et al. | |
| 5,096,885 A | 3/1992 | Pearlman et al. | |
| 5,215,743 A | 6/1993 | Singh et al. | |
| 5,252,480 A | 10/1993 | Yokota et al. | |
| 5,262,296 A | 11/1993 | Ogawa et al. | |
| 5,328,694 A | 7/1994 | Schwinn | |
| 5,399,670 A | 3/1995 | Bhattacharya et al. | |
| 5,580,856 A | 12/1996 | Prestrelski et al. | |
| 5,608,038 A | 3/1997 | Eibl et al. | |
| 5,612,315 A | 3/1997 | Pikal et al. | |
| 5,849,700 A | 12/1998 | Sorenson et al. | |
| 5,871,736 A | 2/1999 | Bruegger et al. | |
| 5,994,511 A | 11/1999 | Lowman et al. | |
| 6,037,453 A | 3/2000 | Jardieu et al. | |
| 6,096,872 A | 8/2000 | Van Holten et al. | |
| 6,172,213 B1 | 1/2001 | Lowman et al. | |
| 6,252,055 B1 | 6/2001 | Relton | |
| 6,267,958 B1 | 7/2001 | Andya et al. | |
| 6,290,957 B1 | 9/2001 | Lowman et al. | |
| 6,329,509 B1 | 12/2001 | Jardieu et al. | |
| 6,440,426 B1 | 8/2002 | Wheeler et al. | |
| 6,525,102 B1 * | 2/2003 | Chen et al. ................. | 424/85.2 |
| 6,541,606 B2 | 4/2003 | Margolin et al. | |
| 6,638,913 B1 | 10/2003 | Speck et al. | |
| 6,682,735 B2 | 1/2004 | Lowman et al. | |
| 6,685,939 B2 | 2/2004 | Jardieu et al. | |
| 6,685,940 B2 | 2/2004 | Andya et al. | |
| 6,699,472 B2 | 3/2004 | Jardieu et al. | |
| 6,723,833 B1 | 4/2004 | Lowman et al. | |
| 6,875,432 B2 | 4/2005 | Liu et al. | |
| 7,157,085 B2 | 1/2007 | Lowman et al. | |
| 2002/0045571 A1 | 4/2002 | Liu et al. | |
| 2003/0092607 A1 | 5/2003 | Carpenter et al. | |
| 2003/0113316 A1 | 6/2003 | Kaisheva et al. | |
| 2003/0138417 A1 | 7/2003 | Kaisheva et al. | |
| 2004/0019243 A1 | 1/2004 | Nightingale et al. | |
| 2004/0191243 A1 | 9/2004 | Chen et al. | |
| 2004/0197324 A1 | 10/2004 | Liu et al. | |
| 2005/0158303 A1 | 7/2005 | Liu et al. | |
| 2005/0175603 A1 | 8/2005 | Liu et al. | |
| 2006/0051347 A1 | 3/2006 | Winter | |
| 2006/0127395 A1 | 6/2006 | Arvinte et al. | |
| 2007/0053900 A1 * | 3/2007 | Liu et al. ................... | 424/131.1 |
| 2007/0086995 A1 | 4/2007 | Liu et al. | |
| 2007/0116700 A1 | 5/2007 | Liu et al. | |
| 2008/0071063 A1 * | 3/2008 | Allan et al. ................. | 530/387.1 |
| 2009/0060906 A1 * | 3/2009 | Barry et al. ................. | 424/131.1 |
| 2009/0169544 A1 * | 7/2009 | Nilsson et al. ............. | 424/130.1 |
| 2009/0280129 A1 | 11/2009 | Liu et al. | |

FOREIGN PATENT DOCUMENTS

| | | |
|---|---|---|
| CA | 2138853 A1 | 6/1995 |
| CH | 684 164 A5 | 7/1994 |
| EP | 0 025 719 A2 | 3/1981 |
| EP | 0 117 060 A2 | 8/1984 |
| EP | 0 117 060 A3 | 8/1984 |
| EP | 0 187 712 A2 | 7/1986 |
| EP | 0 303 746 A1 | 2/1989 |
| EP | 0 303 746 B1 | 2/1989 |
| EP | 0 303 746 B2 | 2/1989 |
| EP | 0 391 444 A2 | 10/1990 |
| EP | 0 391 444 A3 | 10/1990 |
| EP | 0 531 539 A1 | 3/1993 |
| EP | 0 531 539 B1 | 3/1993 |
| EP | 0 597 101 A1 | 5/1994 |
| EP | 0 597 101 B1 | 5/1994 |

(Continued)

OTHER PUBLICATIONS

Breen, E.D. et al., "Effect of Moisture on the Stability of a Lyophilized Humanized Monoclonal Antibody Formulation" *Pharmaceutical Research* 18(9) :1345-1353 (Sep. 2001).

Chang, Liuquan (Lucy), "Mechanisms of Protein Stabilization in the Solid State" *Journal of Pharmaceutical Sciences* 98(9) :2886-2908 (Sep. 2009).

Chen et al., "Influence of histidine on the stability and physical properties of a fully human antibody in aqueous and solid forms" *Pharmaceutical Research* 20(12) :1952-1960 (Dec. 2003).

Cleland et al., "The Development of Stable Protein Formulations: A Close Look at Protein Aggregation, Deamidation, and Oxidation" *Critical Reviews in Therapeutic Drug Carrier Systems* 10(4) :307-377 (1993).

Daugherty, et al., "Formulation and delivery issues for monoclonal antibody therapeutics" *Advanced Drug Delivery Reviews* 58:686-706 (2006).

Garidel, et al., "A thermodynamic analysis of the binding interaction between polysorbate 20 and 80 with human serum albumins and immunoglobulins: A contribution to understand colloidal protein stabilisation" *Biophysical Chemistry* 143:70-78 (2009).

(Continued)

*Primary Examiner* — Elly-Gerald Stoica

(74) *Attorney, Agent, or Firm* — Morrison & Foerster LLP

(57) ABSTRACT

A formulation comprising a therapeutically effective amount of an antibody, optionally, not subjected to prior lyophilization, a buffer maintaining the pH in the range from about 4.5 to about 6.5, and an optional surfactant is described, along with uses for such a formulation.

44 Claims, 5 Drawing Sheets

FOREIGN PATENT DOCUMENTS

| | | |
|---|---|---|
| EP | 0 661 060 A2 | 7/1995 |
| EP | 0 661 060 A3 | 7/1995 |
| EP | 0 661 060 B1 | 7/1995 |
| EP | 0 764 447 A2 | 3/1997 |
| EP | 0 787 497 A2 | 8/1997 |
| EP | 0 787 497 A3 | 8/1997 |
| EP | 0 841 067 A1 | 5/1998 |
| EP | 0 841 067 B1 | 5/1998 |
| EP | 0 909 564 A1 | 4/1999 |
| EP | 0 909 564 B1 | 4/1999 |
| EP | 1 197 221 A1 | 4/2002 |
| EP | 1 197 221 B1 | 4/2002 |
| EP | 1 325 751 A1 | 7/2003 |
| EP | 1 356 829 A2 | 10/2003 |
| EP | 2 335 725 A1 | 6/2011 |
| GB | 2 030 150 A | 4/1980 |
| JP | 5-504342 | 7/1993 |
| JP | 7-206709 A | 8/1995 |
| JP | 11-510170 A | 9/1999 |
| JP | 2001-503781 A | 3/2001 |
| WO | WO-89/11297 A1 | 11/1989 |
| WO | WO-90/11091 A1 | 10/1990 |
| WO | WO-92/17207 A1 | 10/1992 |
| WO | WO-93/04173 A1 | 3/1993 |
| WO | WO-93/05799 A1 | 4/1993 |
| WO | WO-95/23854 A1 | 9/1995 |
| WO | WO-96/20202 A1 | 4/1996 |
| WO | WO-97/04801 A1 | 2/1997 |
| WO | WO-97/45140 A1 | 4/1997 |
| WO | WO-97/26862 A2 | 7/1997 |
| WO | WO-97/26909 A1 | 7/1997 |
| WO | WO-97/28828 A1 | 8/1997 |
| WO | WO-98/22136 A2 | 5/1998 |
| WO | WO-98/22136 A3 | 5/1998 |
| WO | WO-99/01556 A2 | 1/1999 |
| WO | WO-99/01556 A3 | 1/1999 |
| WO | WO-00/15260 A1 | 3/2000 |
| WO | WO-01/24814 A1 | 4/2001 |
| WO | 02/12501 | 2/2002 |
| WO | WO-02/30463 A2 | 4/2002 |
| WO | WO-02/30463 A3 | 4/2002 |
| WO | WO-02/30464 A1 | 4/2002 |
| WO | WO-02/072636 A2 | 9/2002 |
| WO | WO-02/072636 A3 | 9/2002 |
| WO | WO-02/096457 A2 | 12/2002 |
| WO | WO-02/096457 A3 | 12/2002 |
| WO | WO-03/009817 A2 | 2/2003 |
| WO | WO-03/039485 A2 | 5/2003 |
| WO | WO/2004/030607 * | 4/2004 |
| WO | WO-2004/091658 A1 | 10/2004 |
| WO | WO-2006/065746 A2 | 6/2006 |
| WO | WO-2006/065746 A3 | 6/2006 |

OTHER PUBLICATIONS

He, et al., "High throughput Thermostability Screening of Monoclonal antibody formulations" *Journal of Pharmaceutical Sciences* 99(4) :1707-1720 (Apr. 2010).

Manning, et al., "Stability of Protein Pharmaceuticals: An Update" *Pharmaceutical Research* 27(4) :544-575 (Apr. 2010).

Mattern, et al., "Formulation of proteins in vacuum-dried glasses. II. Process and storage stability in sugar-free amino acid Systems" *Pharmaceutical Development and Technology* 4(2) :199-208 (1999).

Patapoff, et al., "Polysorbate 20 prevents the precipitation of a monoclonal antibody during shear" *Pharmaceutical Development and Technology* 14(6) :659-664 (2009).

Tian, et al., "Calorimetric investigation of protein/amino acid interactions in the solid state" *International Journal of Pharmaceutics* 310:175-186 (2006).

Tian, et al., "Spectroscopic evaluation of the stabilization of humanized monoclonal antibodies in amino acid formulations" *International Journal of Pharmaceutics* 335:20-31 (2007).

Adelroth, E. et al. (Aug. 2000). "Recombinant Humanized mAb-E25, an Anti-IgE mAb, in Birch Pollen-induced Seasonal Allergic Rhinitis," *J. Allergy Clin. Immunol.* 106(2):253-259, Abstract Only.

American Hospital Formulary Service. (1998). "Immune Globulin," *AHFS 98 Drug Information*, American Hospital Formulary Service, pp. 2708-2717.

Anonymous. (May 14, 2004). "Gammanorm® Receives Approval in 9 More Countries," Octapharma News, located at <http://www.octapharma.com/corporate/01_octapharma_news/02_news_2004/051604/...>, last visited Jun. 16, 2010, two pages.

Anonymous. "Calculation of the Salt and/or Buffer Concentration of Beriglobin®," Excerpt/Analysis from WO 97/04801, two pages.

Anonymous. Excerpt from Irish Marking Authorization Application in document dated Jan. 13, 1983, 2010, Product Description of "Gammabulin," four pages.

Anonymous. Properties of "Beriglobin," Excerpt/Analysis from WO 97/04801, one page.

Anonymous. Vikositäts-Tabelle., one page. English Description: Viscosity table, the compilation in accordance with D17 (this table) shows the viscosities of the preparations mentioned in citations D3 (EP 0 187 712) and D4 (EP 0 025 719) and the preparations in accordance with D5 (Austria-Codex: Beriglobin) and D8 (Pharmacia: Gammanorm).

Anonymous. Vikositäts-Tabelle, with English Translation, two pages. (D17 in Octapharma EP Opposition). (Document No. 21 on Aug. 10, 2010 SB/08).

Arakawa et al. (1991). "Protein-Solvent Interactions in Pharmaceutical Formulations" *Pharmaceutical Research* 8(3):285-291.

Austria-Codex. (1997). Definition of "Beriglobin" in Austria-Codex Fachinformation, pp. 354-355. (Foreign Language with English Translation four pages.).

Austria-Codex. (1997). Definition of "Berirab" in Austria-Codex Fachinformation, pp. 360-361. (Foreign Language with English Translation, four pages.).

Austria-Codex. (1997). Definition of "Tetagam" in Austria-Codex Fachinformation, pp. 3198-3199. (Foreign Language with English Translation, five pages.).

Bam, N.B. et al. (1995). "Stability of Protein Formulations: Investigation of Surfactant Effects by a Novel EPR Spectroscopic Technique," *Pharmaceutical Research* 12:2-11.

Bayer Corporation. (Oct. 2000). Product Description of BayHep B®, seven pages.

Bayer NZ (Oct. 5, 2004). Datasheet: BayHep B, 10 pages.

Behring, CSL. Package Insert Product Description of "Beriglobin®," two pages. (Foreign Language. With English Translation, eight pages.).

Benninger, G.W. et al. (Aug. 1971). "Aggregation Phenomenon in an IgG Multiple Myeloma Resulting in the Hyperviscosity Syndrome," *American Journal of Medicine* 51:287-293.

Booth, F. (1950). "The Electroviscous Effect for Suspensions of Solid Sperical Particles," *Proc. Roy. Soc . (London)* A203:533-551.

British Pharmacopoeia. (Dec. 1, 1999). vol. II, pp. A110, Appendix I D, 2101, and A82 Appendix I A, four pages.

Buzzell, J.G. et al. (Sep. 1956). "The Effect of Charge and Ionic Strength on the Viscosity of Ribonuclease," *J. Phys. Chem.* 60:1204-1207.

Capra, J.D. et al. (1970). "Aggregation of γG3 Proteins: Relevance to the Hyperviscosity Syndrome," *The Journal of Clinical Investigation* 49:610-621.

Carpenter et al. (1997). "Rational Design of Stable Lyophilized Protein Formulations: Some Practical Advice," *Pharmaceutical Research* 14(8):969-975.

Casale, T.B. (Oct. 2001). "Anti-Immunoglobulin E (Omalizumab) Therapy in Seasonal Allergic Rhinitis," *Am. J. Respir. Crit. Care Med.* 164(8):S18-S21, located at <http://ajrccm.atsjournals.org/cgi/content/full/164/8/S1/S18>, last visited Jun. 7, 2010, 7 pages.

Casolaro, V. et al. (1993). "Release from Human Basopbils and Mast Cells" *J. of Pharmacology and. Experimental Therapeutics* 267(3):1375-1385.

Centocor, Inc. (Aug. 12, 1998). Product Description of Remicade™ Infliximab for IV Injection, 12 pages.

Chen, B. et al. (Dec. 2003). "Influence of Histidine on the Stability and Physical Properties of a Fully Human Antibody in Aqueous and Solid Forms," *Pharmaceutical Research* 20(12):1952-1960.

Chick, H. (1914). Chapter XXXIV, "The Viscosity of Protein Solutions. II. Pseudoglobulin and Euglobulin (Horse)," *Biochem J.* 8:261-280.

Cleland, J.L. et al. (1995). "Development of Stable Protein Formulations for Microencapsulation in Biodegradable Polymers," *Proceed. Intern. Symp. Control. Rel. Bioact. Mater.* 22:514-515.

Corne, J. et al. (Mar. 1997). "The Effect of Intravenous Administration of a Chimeric Anti-IgE Antibody on Serum IgE Levels in Atopic Subjects: Efficacy, Safety, and Pharmacokinetics," *J. Clin. Invest.* 99(5):879-887.

Dalakas, M.C. (Feb. 1994). "High-dose Intravenous Immunoglobulin and Serum Viscosity: Risk of Precipitating Thromboembolic Events," *Neurology* 44:223-226.

Dalakas, M.C. (May 1, 1997). "Intravenous Immune Globulin Therapy for Neurologic Diseases," *Annals of Internal Medicine* 126(9):721-730.

Dalakas, M.C. (1998). "Mechanism of Action of Intravenous Immunoglobulin and Therapeutic Considerations in the Treatment of Autoimmune Neurologic Diseases," *Neurology* 51(Suppl. 5):S2-S8.

Doutrelepont, J.M. et al. (1991). "Hyper IgE in Stimulatory Graft-versus-Hot Disease: Role of Interleukin-4," *Clin. Exp. Immunol.* 83:133-136.

Dráber, P. et al. (1995). "Stability of Monoclonal IgM Antibodies Freeze-Dried in the Presence of Trehalose," *Journal of Immunological Methods* 181(1):37-43.

Fachinfo-Service. (Oct. 2009). "Baxter: SUBCUVIA 160 g/l Injektionslösung," "Package Circular: Baxter SUBCUBIA 160 g/l Solution for Injection," *Fachinformation Rote Liste*, three pages, with English Translation, six pages.

Fachinfo-Service. (Apr. 2010). "CSL Behring: Beriglobin®," "Package Circular: CSL Behring: Beriglobin®,":*Fachinformation Rote Liste*, three pages, with English Transation six pages.

Fahey, K.R. et al. (Dec. 1938). "The Viscosities of Solutions of the Proteins of Horse Serum," *Journal of American Chem. Society* 60:3039-3043.

Giles, R.L. et al. (1990). "Plastic Packaging Materials," Chapter 80 in *Remington's Pharmaceutical Sciences*, 18$^{th}$ Edition, Gennaro, A.R. ed., Mack Publishing Company: Easton, PA, p. 1499.

Gokarn, Y.R. et al. (Aug. 2008). "Self-Buffering Antibody Formulations," *Journal of Pharmaceutical Sciences* 97(8):3051-3066.

Haag, S. et al. (Oct. 2006). "Comparison of the Viscosity of Three Subcutaneous Immunoglobulin Brands (SCIG). Potential Implicatons for Clinical Use," Poster *presentation at XIIth Meeting of the European Society for Immunodeficiencies*, Oct. 4-7, 2006, Budapest, Hungary, two pages.

Haecker, G. et al. (1994). "Proliferative and Cytolytic Responses of Human γδ T Cells Display a Distinct Specificity Pattern," *Immunology* 81:564-566.

Hankinson, C.L. et al. (1941). "Electrokinetics XXV. The Electroviscous Effect. II In Systems of Calcium and Sodium Caseinates," *J. Phys. Chem.* 45(6):943-953.

Harris, R.J. et al. (2004). "Commercial Manufacturing Scale Formulation and Analytical Characterization of Therapeutic Recombinant Antibodies," *Drug Development Research* 61:137-154.

Hess, E.L. et al. (May 20, 1950). "The Intrinsic Viscosity of Mixed Protein Systems, Including Studies of Plasma and Serum," *J. Gen. Physiol.* 33:511-523.

Holma, B. et al. (1989). "pH- and Protein-Dependent Buffer Capacity and Viscosity of Respiratory Mucus, Their Interrelationships and Influence on Health," *The Science of the Total Environment* 84:71-82.

Hudson, L. et al. (1980). *Practical Immunology*, Second Edition, Blackwell Scientific Publications, p. 336.

IDEC/GENENTECH. (Nov. 1997). Product Description of Rituxan™, two pages.

Immuno, Ltd. (Jan. 13, 1983). Letter from N. Berry to National Drugs Advisory Board re: Authorization to Market Gammabulin, one page.

Immuno, Ltd. (Dec. 20, 1991). Letter of Product Licence Applications for TETABULIN for GB and Ireland, three pages.

Immuno, Ltd. (Oct. 1997). Normal Immunoglobulin Injection B.P.: GAMMABULIN® Package Insert Product Description, two pages.

Immuno, Ltd. (Dec. 1997). GAMMABULIN®: Normal Immunoglobulin Injection B.P. Product Description, two pages.

International Search Report mailed on Jun. 19, 2002, for PCT Application No. PCT/US01/42487, filed on Oct. 4, 2001, two pages.

Iwanaga, S. (1978). "1-2-1 Separation Method Making Use of Solubility," *New Lectures on Experimental Chemistry* 20(Biochemistry 1):14-26, (Japanese language with English Translation, 16 pages).

Jones, A. (1993). "Analysis of Polypeptides and Proteins." *Adv. Drug Delivery Rev.* (10)29-90.

Kalapathy, U. et al. (1996). "Alkali-Modified Soy Proteins: Effect of Salts and Disulfide Bond Cleavage on Adhesion and Viscosity," *JAOCS* 73(8):1063-1066.

Kanai, S. et al. (Oct. 2008). "Reversible Self-Association of a Concentrated Monoclonal Antibody Solution Mediated by Fab-Fab Interaction That Impacts Solution Viscosity," *Journal of Pharmaceutical Sciences* 97(10):4219-4227.

Katdare et al. Appendix: Formulations of Approved Protein Drugs *in Excipients for Protein Drugs, Excipient Development for Pharmaceutical Biotechnology and Drug Delivery Systems*, Gokarn et al. eds., pp. 307-331.

Kim, Y-C. et al. (1997). "Diffusivity, Viscosity, and Cluster Formation in Protein Solutions," *Biotechnol. Bioprocess Eng.* 2(1):64-67.

Kinekawa, Y-I. et al. (1998). "Effects of Salts on the Properties of Sols and Gels Prepared from Whey Protein Isolate and Process Whey Protein," *Journal of Dairy Science* 81(6):1532-1544.

Kistler, P. et al. (1962). "Large Scale Production of Human Plasma Fractions," *Vox Sang* 7:414-424.

Kochwa, S. et al. (Jan. 1966). "Aggregation of IgG Globulin in Vivo. II. Physicochemical Properties of the Isolated Protein," *Biochemistry* 5(1):277-285.

Lehninger, A.L. et al. (1993). "Amino Acids and Peptides," Chapter 5 in *Principles of Biochemistry*, Second Edition, World Publishers: New York, NY, pp. 111-122.

Letter dated Jan. 26, 2009 from Representative Mewburn Ellis in Response to Request for Oral Proceedings in EP Patent Application 01981824.4, six pages.

List, P.H. (1985). "Injection and Infusion Preparations," Chapter 18.4, *in Pharmacy: Textbooks for Pharmacists*, 4$^{th}$ Edition, Scientific Publishers: Stuttgart, DE, pp. 416-419. (With English Translation, six pages).

Liu, J. et al. (Sep. 2005). "Reversible Self-Association Increases the Viscosity of a Concentrated Monoclonal Antibody in Aqueous Solution" *Journal of Pharmaceutical Sciences* 94(9).

Loeb, J. (1921). "Donnan Equilibrium and the Physical Properties of Proteins," Chapter IV, Viscosity, *in The Journal of General Physiology*, pp. 73-95.

Loeb, J. (1921). "Ion Series and the Physical Properties of Proteins," in Chapter III, The Action Salts in Low Concentration, *in The Journal of General Physiology*, pp. 391-414.

Loeb, J. (1921). "Donnan Equilibrium and the Physical Properties of Proteins," Chapter III, Viscosity, *in The Journal of General Physiology*, pp. 827-841.

Mackenzie, M.R. et al. (1970). "The Hyperviscosity Syndrome. I. In IgG Myeloma. The Role of Protein Concentration and Molecular Shape," *The Journal of Clinical Investigation* 49:15-20.

Mahler, H.R. et al. (1966). *Biological Chemisry*, Harper & Row Publishers, Inc.: New York, NY, Table 2.1, one page.

Martindale. (1993). Descriptions of "Normal Immunoglobins" *in Martindale The Extra Pharmacopoeia*, 30$^{th}$ Edition, Reynolds, J.E.F. ed., Pharmaceutical Press: London, England, pp. 1290-1294, 1302-1303, 1578, 1611, 1856.

Martindale. (1999). Descriptions of "Normal Immunoglobins" *in Martindale The Complete Drug Reference*32$^{nd}$ Edition, Parfitt, K. ed., Pharmaceutical Press: London, England, pp. 1522-1525, 1535, 1778, 1805, 1932, 2011.

Menjivar, J.A. et al. (1980). "Viscoelastic Effects in Concentrated Protein Dispersions," *Rheol. Acta* 19:212-219.

Merck Index (1983). 10th Ed., Merck &Co., Inc. pp. 797-798.

Middaugh, C.R. et al. (1992). "Protein Solubility," Chapter 4 *in Stability of Protein Pharmaceuticals, Part A: Chemical and Physical Pathways of Protein Degradation*, Ahern, T.J. et al. eds., Plenum Press: New York, NY, pp. 109-134.

Middleton, H.M. III (1979). "Intestinal Absorption of Pyridoxal-5'-Phosphate: Disappearance from Perfused Segments of Rat Jejunum in Vivo," *Journal of Nutrition* 109:975-981.

Milgrom, H. et al. (Dec. 23, 1999). "Treatment of Allergic Asthma with Monoclonal Anti-IgE Antibody. rhuMAb-E25 Study Group," *The New England Journal of Medicine* 341(26):1966-1973.

Milgrom, H. et al. (Aug. 2, 2001). "Treatment of Childhood Asthma With Anti-Immunoglobulin E Antibody (Omalizumab)," *Pediatrics* 108(2):1-10.

Monkos, K. (1997). "Concentration and Temperature Dependence of Viscosity in Lysozyme Aqueous Solutions," *Biochimica et Biophysica Acta* 1339:304-310.

Monkos, K. et al. (1999). "A Comparative Study on Viscosity of Human, Bovine and Pig IgG Immunoglobulins in Aqueous Solutions," *International Journal of Biological Macromolecules* 26:155-159.

Monkos, K. (2000). "Viscosity Analysis of the Temperature Dependence of the Solution Conformation of Ovalbumin," Biophysical Chemistry 85:7-16.

Nielsen, K. et al. (1995). "Stability of Freeze Dried Horseradish Peroxidase Conjugated Monoclonal Antibodies Used in Diagnostic Serology," *Journal of Immunoassay* 16(2):183-197.

Non-Final Office Action mailed on Dec. 21, 2010, for U.S. Appl. No. 12/197,005, filed on Aug. 22, 2008, eight pages.

Notice of Opposition and Opposition Brief for EP 1 324 776: Abbott Bioresearch Center Patent Department, Jun. 16, 2010, 24 pages.

Notice of Opposition and Opposition Brief for EP 1 324 776: Maiwald, Jun. 16, 2010, 77 pages.

Notice of Opposition of EP 1 324 776: ABLYNX N.V., Jun. 16, 2010, seven pages.

Notice of Opposition of EP 1 324 776: ARECOR Limited, Jun. 15, 2010, five pages.

Notice of Opposition of EP 1 324 776: Baxter Healthcare SA, Jun. 16, 2010, six pages.

Notice of Opposition of EP 1 324 776: Boehringer Ingelheim Pharma GMBH & Co., Jun. 16, 2010, seven pages.

Notice of Opposition of EP 1 324 776: Maiwald/Eingabe, Jun. 16, 2010, one page.

Notice of Opposition of EP 1 324 776: Sanofi Aventis, Jun. 16, 2010, seven pages. (Foreign Language).

Notice of Opposition of EP 1 324 776: Synthon B.V., Jun. 16, 2010, six pages.

Notice of Opposition of EP 1 324 776: UCB Pharma S.A., Jun. 15, 2010, four pages.

Nydegger, U.E. (1996). "Safety and Side Effects of I.V. Immunoglobulin Therapy," *Clinical and Experimental Rheumatology* 14(Suppl. 15):S53-S57.

Octapharma. (Jan. 9, 2008). Product Description of Gammanorm, Octapharma, eight pages.

Office Action Response for EP Application No. 01981824.4 filed by Mewburn Ellis, Oct. 11, 2004, 14 pages.

Opposition Brief Filed by Ablynx N.V. in EP 1 324 776 filed on Jun. 16, 2010, 17 pages.

Opposition Brief Filed by Baxter Healthcare Corporation in EP 1 324 776 filed on Jun. 16, 2010, 39 pages.

Opposition Brief Filed by Boehringer Ingelheim Pharma in EP 1 324 776 filed on Jun. 16, 2010, 11 pages.

Opposition Brief Filed by Octapharma AG in EP 1 324 776 filed on Jun. 16, 2010, 11 pages. (English Language).

Opposition Brief Filed by Octapharma AG in EP 1 324 776 filed on Jun. 16, 2010, 14 pages. (German Language).

Opposition Brief Filed by Sanofi Aventis in EP 1 324 776 filed on Jun. 16, 2010, 12 pages. (English Language).

Opposition Brief Filed by Sanofi Aventis in EP 1 324 776 filed on Jun. 16, 2010, 13 pages. (French Language).

Opposition Brief Filed by Synthon in EP 1 324 776 filed on Jun. 16, 2010, nine pages.

Opposition Brief Filed by UCB Celltech in EP 1 324 776 filed Jun. 2010, 31 pages.

Opposition Brief Filed by UCB Pharma in EP 1 324 776, filed on Jun. 15, 2010, 23 pages.

Osmolalität: Osmology Data of Antibody Solutions, one page. (Foreign Language with English Translation, two pages).

Pearlman et al. (1991). "Analysis of Protein Drugs," Chapter 6 in *Peptide and Protein Drug Delivery*, Vincent H. L. Lee ed., Marcel Dekker, Inc., pp. 247-301.

Pei. "Immunoglobulinpräparate" located at <http://www.pei.de/cln_101/nn_158990/DE/arzneimittel/immunoglobuline/im-iv-sk/im-i...>, last visited Jun. 16, 2010, three pages. (Foreign Language with English Translation, six pages).

Perepetschkina, N.P. et al. (1986). "Some Specific Features of the Ultrafiltration of Immunobiologic Preparations," *The Mechnikov Central Research Institute of Vaccines and Serums*, 6:46-50. (Russian Language with English Translation, six pages).

Pharmacia. (Oct. 17, 1994). Composition and Product Description of "Gammanorm", four pages. (Foreign Language).

Pharmacia. (Oct. 17, 1994). Registration Application, Composition and Product Description of "Gammanorm", with English Translation, eight pages.

Physica. Graphic Representation of Viscosity Measurement of Beriglobin®, *Physica*.

Physicians' Desk Reference. (1999). Product Descriptions of Baxter Healthcare products, *Physicians' Desk Reference*, 53$^{rd}$ Edition, Medical Economics Company, Inc., Montvale: NJ, pp. 621-623, 684-690, and 2082-2085.

Pikal et al. (1991) "The Effects of Formulation Variables on the Stability of Freeze-Dried Human Growth Hormone," *Pharmaceutical Research* 8:427-436.

Press Release. (Jun. 19, 2000). "7,500 Pharmaceutical Scientists to Explore Therapies for New Millennium," *AAPS PressRoom*, located at <http://www.aapspharmaceutica.com/about/press/newsrelea...>, last visited Apr. 12, 2010, one page.

Presta, L.G. et al. (Sep. 1, 1993). "Humanization of an Antibody Directed Against IgE" *J. Immunol.* 151(5):2623-2632.

Priority Document, GB0113179.6, of WO 02/096457, dated Aug. 15, 2002.

Reinhart, W.H. et al. (Mar. 14, 1992). "Effect of High-Dose Intravenous Immunoglobulin Therapy on Blood Rheology," *The Lancet* 339:662-664.

Rote Liste®. (1997). Description of "Sera, Immunglobuline u. Impfstoffe," in Rote List®, two pages. (German Language with English Translation four pages.).

Rote Liste®. (1999_A). Description of "Sera, Immunglobuline u. Impfstoffe," in Rote List®, two pages. (German Language with English Translation, three pages).

Rote Liste®. (1999_B). Description of "Sera, Immunglobuline u. Impfstoffe," in Rote List®, two pages. (German Language with English Translation, three pages).

Rote Liste®. (1999-C). Description of "Sera, Immunglobuline u. Impfstoffe," in Rote List®, two pages. (German Language with English Translation, three pages).

Rote Liste®. (2004). Description of "Sera, Immunglobuline u. Impfstoffe," in Rote List®, two pages. (German Language with English Translation, four pages).

Saluja, A. et al. (2008). "Nature and Consequences of Protein-Protein Interactions in High Protein Concentration Solutions," *International Journal of Pharmaceutics* 358:1-15.

Sampson, H.A. (2000). "Food Anaphylaxis," *British Medical Bulletin* 56(4):925-935.

Schneider, C. et al. (1990). "Some Viscosity Characteristics of Faba Bean Protein Isolats within a pH Range Relevant for Foods," *Die Nahrung* 34(8):735-745.

Schultz, J.S. et al. (Jan. 1979). "Reflection Coefficients of Homopore Membranes: Effect of Molecular Size and Configuration," *J. Gen. Physiol.* 73:49-60.

Siegel, F.P. (1990). "Tonicity, Osmoticity, Osmolality and Osmolarity," Chapter 79 in *Remington's Pharmaceutical Sciences*, 18$^{th}$ Edition, Gennaro, A.R. ed., Mack Publishing Company: Easton, PA, pp. 1481-1498.

Simons, F.E.R. (2003). "What's in a Name? The Allergic Rhinitis—Asthma Connection," *Clinical and Experimental Alleergy Reviews* 3(1):9-17.

Stokke, B.T. et al. (1981). "Human Spectrin. VI. A Viscometric Study," *Biochimica et Biophysica Acta* 640:640-645.

Tanford, C. et al. (Feb. 1956). "The Viscosity of Aqueous Solutions of Bovine Serum Albumin Between pH 4.3 and 10.5," *J. Phys. Chem.* 60:225-231.

Teschner, W. (Jun. 16, 2010). Technical Expert Declaration, with Exhibits 1-5, 10 pages.

Trissel, L.A. (1998). "Immune Globulin Intravenous AHFS 80:04," in *Handbook of Injectable Drugs*, 10th Edition, American Society of Health-System Pharmacists: Bethesda, MD, pp. 676-677.

Tsumoto, K. et al. (Jul. 17-19, 2003). "Magic Agent for Protein Refolding and Solubilization: Arginine," *2003 Colorado Protein Stability Conference*, presented by the University of Colorado Center for the Pharmaceutical Biotechnology, Breckenridge, Colorado, two pages.

U.S. Appl. No. 60/240,107, filed Oct. 12, 2000, by Lui et al.

U.S. Appl. No. 60/293,834, filed May 24, 2001, by Lui et al.

U.S. Appl. No. 60/460,659, filed Apr. 4, 2003, by Liu et al.

U.S. Appl. No. 12/197,005, filed Aug. 22, 2008, by Liu et al.

U.S. Appl. No. 12/573,801, filed Oct. 5, 2009, by Liu et al.

Vandersande, J. (Jun. 15, 2010). Technical Expert Declaration, with Exhibits 1-7, 20 pages.

Vladutiu, A.O. et al. (1991). "Polyclonal Gammopathy with Marked Increase in Serum Viscosity," *Clin. Chem.* 37(10):1788-1793.

Wagner, J.R. et al. (1992). "Effect of Physical and Chemical Factors on Rheological Behavior of Commercial Soy Protein Isolates: Protein Concentration, Water Imbibing Capacity, Salt Addition, and Thermal Treatment," *J. Agric. Food Chem.* 40:1930-1937.

Wang, Y-C. et al. (1988) "Parentera Formulations of Proteins and Peptides: Stability and Stabilizers," *J. Parenteral Sci. Tech.* (Technical Report No. 10)42(2S):S4-S26.

Wang, W. (1999). "Instability, Stabilization, and Formulation of Liquid Protein Pharmaceuticals," *International Journal of Pharmaceutics* 185:129-188.

Wang, N. et al. (Apr. 2009). "Opalescence of an IgG1 Monoclonal Antibody Formulation is Mediated by Ionic Strength and Excipients," *BioPharm International* pp. 36-47.

Wang, W. et al. (Jan. 2007). "Antibody Structure, Instability, and Formulation," *Journal of Pharmaceutical Sciences* 96(1):1-26.

Warren, J.R. et al. (Aug. 25, 1970). "Denaturation of Globular Proteins: II. The Interaction of Urea with Lysozyme," *The Journal of Biological Chemistry* 245(16):4097-4104.

White, A. et al. (1964). Principles of Biochemistry, 3rd edition, McGraw-Hill Company pp. 540.

Wikipedia. (2010). Definition of "Viscosity," *Wikipedia, the Free Encyclopedia*, located at <http://en.wikipedia.org.wiki/Viscosity>, last visited Jun. 11, 2010, 56 pages (includes history of revisions).

Wikipedia. (2010). "Reference Ranges for Blood Tests," *Wikipedia, the Free Encyclopedia*, located at <http://en.wikipedia.org.wiki/Reference_ranges_for_blood_tests>, last visited Jun. 3, 2010, 16 pages.

Xu, X. et al. (1995). "Expression of Functional Insulin-Like Growth Factor-1 Receptor on Lymphoid Cell Subsets of Rats," *Immunology* 85:394-399.

Yardimci, A. (Jun. 15, 2010). Technical Expert Declaration, with Exhibits 1-3, 15 pages.

Yousef, M.A. et al. (1998). "Free-Solvent Model of Osmotic Pressure Revisited: Application to Concentrated IgG Solution under Physiological Conditions," *Journal of Colloid and Interface Science* 197:108-118.

Zietkiewicz et al. (1971). "In Vivo Studies on the Action on the Tissue of the Osmolality of Administered Drugs." *Grzyby Drozdzopodobne*. (English Translation Attached) 23:869-870.

Notice of Opposition and Brief, mailed on Jun. 10, 2011, for EP Patent No. 1 610 820, filed on Mar. 29, 2004, twenty-nine pages.

Letter dated Jul. 6, 2011, Represenative Müller Fottner Steinecke further to Opposition Brief for EP Patent No. 1 610 820, sixty-three pages.

European Patent Office Communciation mailed Nov. 25, 2011, for EP Patent No. 1 610 820, filed Mar. 29, 2004, three pages.

European Patent Office Communication mailed on Jan. 25, 2012, for EP Patent No. 1 610 820, filed on Mar. 29, 2004, twelve pages.

European Patent Office Communication mailed on Mar. 1, 2012, for EP Patent No. 1 610 820, filed on Mar. 29, 2004, three pages.

\* cited by examiner

2-D03-VH (SEQ ID NO: 1)
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCAAGTATTAGTGTTGGTGGACATAGGACATATTAT
GCAGATTCCGTGAAGGGCCGGTCCACCATCTCCAGAGACAATTCCAAGAACACGCTGTAT
CTGCAAATGAACAGCCTGAGAGCCGAGGACACTGCCGTGTATTACTGTGCACGGATACGG
GTGGGTCCGTCCGGCGGGGCCTTTGACTACTGGGGCCAGGGTACACTGGTCACCGTGAGC
TCA

2-D03-VL (SEQ ID NO: 2)
CAGTCTGTGCTGACTCAGCCACCCTCAGCGTCTGGGACCCCCGGGCAGAGGGTCACCAT
CTCCTGCTCTGGAAGCAACACCAACATTGGGAAGAACTATGTATCTTGGTATCAGCAGC
TCCCAGGAACGGCCCCCAAACTCCTCATCTATGCTAATAGCAATCGGCCCTCAGGGGTC
CCTGACCGATTCTCTGGCTCCAAGTCTGGCACCTCAGCCTCCCTGGCCATCAGTGGGCT
CCGGTCCGAGGATGAGGCTGATTATTACTGTGCGTCATGGGATGCCAGCCTGAATGGTT
GGGTATTCGGCGGAGGAACCAAGCTGACGGTCCTAGGT

FIG. 1

2-D03-VH (SEQ ID NO: 3)
EVQLLESGGGLVQPGGSLRLSCAASGFTFSNAWMSWVRQAPGKGLEWVSSISVGGHRTYYA
DSVKGRSTISRDNSKNTLYLQMNSLRAEDTAVYYCARIRVGPSGGAFDYWGQGTLVTVSS

2-D03-VL (SEQ ID NO:4)
QSVLTQPPSASGTPGQRVTISCSGSNTNIGKNYVSWYQQLPGTAPKLLIYANSNRPSGVPDRF
SGSKSGTSASLAISGLRSEDEADYYCASWDASLNGWVFGGGTKLTVLG

IgG1-CH (SEQ ID NO:6)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVM
HEALHNHYTQKSLSLSPGK

IgG1-CL (SEQ ID NO:7)
QPKAAPSVTLFPPSSEELQANKATLVCLISDFYPGAVTVAWKADSSPVKAGVETTTPSKQSNN
KYAASSYLSLTPEQWKSHRSYSCQVTHEGSTVEKTVAPTECS

FIG. 2

```
                       SEQUENCE LISTING

<160> NUMBER OF SEQ ID NOS: 9

<210> SEQ ID NO 1
<211> LENGTH: 363
<212> TYPE: DNA
<213> ORGANISM: Artificial Sequence
<220> FEATURE:
<223> OTHER INFORMATION: sequence is synthesized

<400> SEQUENCE: 1
gaggtgcagc tgttggagtc tggggggaggc ttggtacagc ctgggggtc cctgagactc        60 tcctgtgcag cctctggatt caccttcagt aacgcctgga tgagctgggt ccgccaggct       120
ccagggaagg ggctggagtg ggtctcaagt attagtgttg gtggacatag gacatattat       180
gcagattccg tgaagggccg gtccaccatc tccagagaca attccaagaa cacgctgtat       240
ctgcaaatga acagcctgag agccgaggac actgccgtgt attactgtgc acggatacgg       300
gtgggtccgt ccggcggggc ctttgactac tggggccagg gtacactggt caccgtgagc       360
``` tca                                                                 363

<210> SEQ ID NO 2
<211> LENGTH: 333
<212> TYPE: DNA
<213> ORGANISM: Artificial Sequence
<220> FEATURE:
<223> OTHER INFORMATION: sequence is synthesized

<400> SEQUENCE: 2
cagtctgtgc tgactcagcc accctcagcg tctgggaccc ccgggcagag ggtcaccatc    60
tcctgctctg gaagcaacac caacattggg aagaactatg tatcttggta tcagcagctc   120
ccaggaacgg cccccaaact cctcatctat gctaatagca atcggccctc aggggtccct   180
gaccgattct ctggctccaa gtctggcacc tcagcctccc tggccatcag tgggctccgg   240
tccgaggatg aggctgatta ttactgtgcg tcatgggatg ccagcctgaa tggttgggta   300
ttcggcggag gaaccaagct gacggtccta ggt                                333

<210> SEQ ID NO 3
<211> LENGTH: 121
<212> TYPE: PRT
<213> ORGANISM: Artificial Sequence
<220> FEATURE:
<223> OTHER INFORMATION: sequence is synthesized

<400> SEQUENCE: 3

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Ser Ser Ile Ser Val Gly Gly His Arg Thr Tyr Tyr Ala Asp Ser Val
     50                  55                  60

Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser
        115                 120

<210> SEQ ID NO 4
<211> LENGTH: 111
<212> TYPE: PRT
<213> ORGANISM: Artificial Sequence
<220> FEATURE:
<223> OTHER INFORMATION: sequence is synthesized

<400> SEQUENCE: 4

Gln Ser Val Leu Thr Gln Pro Pro Ser Ala Ser Gly Thr Pro Gly Gln
  1               5                  10                  15

Arg Val Thr Ile Ser Cys Ser Gly Ser Asn Thr Asn Ile Gly Lys Asn
             20                  25                  30

Tyr Val Ser Trp Tyr Gln Gln Leu Pro Gly Thr Ala Pro Lys Leu Leu
         35                  40                  45

Ile Tyr Ala Asn Ser Asn Arg Pro Ser Gly Val Pro Asp Arg Phe Ser
     50                  55                  60

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ser Trp Asp Ala Ser Leu
                 85                  90                  95

Asn Gly Trp Val Phe Gly Gly Gly Thr Lys Leu Thr Val Leu Gly
            100                 105                 110

<210> SEQ ID NO 5
<211> LENGTH: 20
<212> TYPE: PRT
<213> ORGANISM: Artificial Sequence
<220> FEATURE:
<223> OTHER INFORMATION: sequence is synthesized

<400> SEQUENCE: 5

Ile Glu Ile Gly Leu Glu Gly Lys Gly Phe Glu Pro Thr Leu Glu Ala
 1               5                  10                  15

Leu Phe Gly Lys
            20

<210> SEQ ID NO 6
<211> LENGTH: 330
<212> TYPE: PRT
<213> ORGANISM: Artificial Sequence
<220> FEATURE:
<223> OTHER INFORMATION: sequence is synthesized

<400> SEQUENCE: 6

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

-continued

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 7
<211> LENGTH: 105
<212> TYPE: PRT
<213> ORGANISM: Artificial Sequence
<220> FEATURE:
<223> OTHER INFORMATION: sequence is synthesized

<400> SEQUENCE: 7

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 8
<211> LENGTH: 6
<212> TYPE: DNA
<213> ORGANISM: Artificial Sequence
<220> FEATURE:
<223> OTHER INFORMATION: sequence is synthesized
<220> FEATURE:
<221> NAME/KEY: modified_base
<222> LOCATION: 2
<223> OTHER INFORMATION: n = A,T,C or G
<220> FEATURE:
<221> NAME/KEY: CAAT_signal
<222> LOCATION: 1, 2, 3, 4, 5, 6
<223> OTHER INFORMATION: CAAT box

<400> SEQUENCE: 8 cncaat                                                          6

<210> SEQ ID NO 9
<211> LENGTH: 6
<212> TYPE: DNA
<213> ORGANISM: Artificial Sequence
<220> FEATURE:
<223> OTHER INFORMATION: sequence is synthesized
<220> FEATURE:
<221> NAME/KEY: PolyA_signal
<222> LOCATION: 1, 2, 3, 4, 5, 6
```

-continued

```
<223> OTHER INFORMATION: polyadenylation signal

<400> SEQUENCE: 9 aataaa                                                               6
```

ANTI-OXIDIZED LDL ANTIBODY FORMULATION

RELATED APPLICATIONS

This application claims priority to and the benefit of U.S. Provisional Application Ser. No. 61/158,331, filed Mar. 6, 2009, the specification of which is incorporated herein in its entirety.

FIELD OF THE INVENTION

This invention is directed to a formulation comprising an antibody.

BACKGROUND

In the past years, advances in biotechnology have made it possible to produce a variety of proteins for pharmaceutical applications using recombinant DNA techniques. Because proteins are larger and more complex than traditional organic and inorganic drugs (e.g., possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (e.g., any process which involves modification of the protein by bond formation or cleavage resulting in a new chemical entity) or physical instability (e.g., changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al *Critical Reviews in Therapeutic Drug Carrier Systems* 10(4): 307-377 (1993).

Included in the proteins used for pharmaceutical applications are antibodies. An example of an antibody useful for therapy is an antibody which binds to oxidized LDL. There is a need in the art for a stable aqueous pharmaceutical formulation comprising an antibody, such as an anti-oxLDL antibody, which is suitable for therapeutic use.

SUMMARY

The invention provides formulations comprising a therapeutically effective amount of an antibody, a buffer maintaining the pH in the range from about 4.5 to about 6.5, and, optionally, a surfactant. In certain embodiments, the formulation is stable at a temperature of about 2-8° C. for at least 12 months. Typically, this results in an aqueous formulation for use, e.g., in pharmaceutical applications. In certain embodiments of the invention, the formulation is a stable aqueous formulation. In certain embodiments, the formulation is a stable aqueous pharmaceutical formulation.

The invention herein relates, at least in part, to the identification of the combination of histidine and arginine, pH 4.5 to 6.5, as a particularly useful buffer for formulating monoclonal antibodies, especially full length antibodies which are susceptible to aggregation. The formulation retards degradation of the antibody product therein. In certain embodiments of the invention, the histidine and arginine buffer is a histidine-acetate and arginine-acetate buffer, pH 5.0 to 6.0. In certain embodiments of the invention, the histidine and arginine buffer is a histidine-succinate and arginine-succinate buffer, pH 4.5 to 6.5. In certain embodiments of the invention, the formulation is sterile.

The formulations of the buffers herein has a pH of 4.5 to 6.5, for example, pH of 5.0 to 6.0, pH 5.25 to 5.75, or pH 5.3 to 5.6. In certain embodiments of the invention, the formulation has a pH of 5.5 or about 5.5. In certain embodiments of the invention, the formulation has a pH of 5.6 or about 5.6.

Thus, in one aspect, the invention concerns a formulation comprising a monoclonal antibody in histidine-acetate and arginine-acetate buffer, pH 4.5 to 6.5. In a further embodiment, it is a, e.g., stable, pharmaceutical formulation.

Thus, in one aspect, the invention concerns a formulation comprising a monoclonal antibody in histidine-succinate and arginine-succinate buffer, pH 4.5 to 6.5. In a further embodiment, it is a, e.g., stable, pharmaceutical formulation.

In certain embodiments, the histidine actetate or histidine succinate concentration in the buffer is from about 5 mM to about 100 mM. In certain embodiments, the histidine acetate or histidine succinate concentration is about 20 mM. In certain embodiments, the arginine acetate or arginine succinate concentration in the buffer is from about 50 mM to about 500 mM. In certain embodiments, the arginine acetate or arginine succinate concentration is about 150 mM.

The formulations herein can optionally comprise a surfactant. In certain embodiments, the surfactant is polysorbate (e.g., polysorbate 20). In certain embodiments, the surfactant concentration is from 0.0001% to about 1.0%. In certain embodiments, the surfactant concentration is from about 0.01% to about 0.1%. In one embodiment, the surfactant concentration is 0.02%. The formulation can optionally comprise methionine (e.g., at a concentration of about 5 mg/ml or 5 mg/ml). The formulation can optionally comprise chelating agent, e.g., EDTA, EGTA, etc. In certain embodiments, the EDTA concentration in the formulation is 1 mM EDTA.

The formulations are typically for an antibody concentration from about 10 mg/ml to about 250 mg/ml. In certain embodiments, the antibody concentration is from about 100 mg/ml to 250 mg/ml. In certain embodiments, the antibody concentration is from about 150 mg/ml to about 200 mg/ml. In certain embodiments, the antibody concentration is from about 25 mg/ml to about 200 mg/ml.

In another aspect, the invention concerns a pharmaceutical formulation comprising: (a) a full length IgG1 antibody susceptible to deamidation or aggregation in an amount from about 10 mg/mL to about 250 mg/mL; (b) histidine-acetate and arginine-acetate buffer, pH 4.5 to 6.5; and (c) polysorbate 20 in an amount from about 0.01% to about 0.1%.

In another aspect, the invention concerns a pharmaceutical formulation comprising: (a) a full length IgG1 antibody susceptible to aggregation in an amount from about 10 mg/mL to about 250 mg/mL; (b) histidine-succinate and arginine-succinate buffer, pH 4.5 to 6.5; and (c) polysorbate 20 in an amount from about 0.01% to about 0.1%.

In certain embodiments, the antibody is a monoclonal antibody. In certain embodiments, the monoclonal antibody is a full length antibody (e.g., IgG1, IgG4, etc.). In certain embodiments, the monoclonal antibody is an antibody fragment (e.g., comprising an antigen binding region). For example, the antibody fragment is a Fab or F(ab')$_2$ fragment. In certain embodiments, the monoclonal antibody is a humanized antibody. In certain embodiments, the monoclonal antibody is susceptible to aggregation. In certain embodiments, the antibody is not subject to prior lyophilization.

In certain embodiments, the monoclonal antibody binds ox-LDL. In yet a further aspect, the invention concerns a pharmaceutical formulation comprising an antibody that binds to ox-LDL in a histidine and arginine buffer at a pH from about 4.5 to about 6.5, and a surfactant. In certain embodiments, the oxLDL antibody comprises the variable heavy and variable light amino acid sequences in SEQ ID Nos. 3 and 4, respectively, of FIG. 2, and optionally, the constant regions (H and L) of SEQ ID Nos: 6 and 7, respectively, of FIG. 2. In certain embodiments, the anti-oxLDL antibody comprises the VH and VL encoded by the nucleic acids of FIG. 1 (SEQ ID NOs: 1 and 2).

The invention also relates to a pharmaceutical formulation comprising ox-LDL antibody in an amount from about 10 mg/mL to about 200 mg/mL, histidine-acetate and arginine-acetate buffer, and polysorbate 20, wherein the pH of the formulation is from about 4.5 to about 6.5.

The invention also relates to a pharmaceutical formulation comprising ox-LDL antibody in an amount from about 10 mg/mL to about 200 mg/mL, histidine-succinate and arginine-succinate buffer, and polysorbate 20, wherein the pH of the formulation is from about 4.5 to about 6.5.

The invention also relates to an article of manufacture comprising a container holding a stable aqueous pharmaceutical formulation comprising a therapeutically effective amount of an antibody, a buffer maintaining the pH in the range from about 4.5 to about 6.5, and, optionally, a surfactant. In certain embodiments of the invention, the buffer is a histidine-acetate and arginine-acetate buffer, pH 5.0 to 6.0. In certain embodiments of the invention, the buffer is a histidine-succinate and arginine-succinate buffer, pH 5.0 to 6.0. In certain embodiments, the pH of the buffer is 5.5. In certain embodiments, the pH of the buffer is 5.6. The invention also concerns a vial with a stopper pierceable by a syringe or a tank (e.g., a stainless steel tank) comprising the formulation inside the vial or tank, optionally in frozen form. In certain embodiments, the vial or tank is stored at about 2-8° C. In certain embodiments, the vial is a 3 cc, 20 cc or 50 cc vial.

Moreover, the invention provides a method of making a pharmaceutical formulation comprising: (a) preparing the monoclonal antibody formulation; and (b) evaluating physical stability, chemical stability, or biological activity of the monoclonal antibody in the formulation.

In yet a further aspect, the invention relates to a method for stabilizing an antibody in an aqueous pharmaceutical formulation by combining a therapeutically effective amount of an antibody, a buffer maintaining the pH in the range from about 4.5 to about 6.5, and, optionally, a surfactant. In certain embodiments of the invention, the buffer is a histidine-acetate and arginine-acetate buffer, pH 4.5 to 6.5. In certain embodiments of the invention, the buffer is a histidine-succinate and arginine-succinate buffer, pH 4.5 to 6.5.

The invention also provides a method for reducing aggregation of a therapeutic monoclonal antibody, comprising formulating the antibody in a histidine-acetate and arginine acetate buffer, pH 4.5 to 6.5. The invention also provides a method for reducing aggregation of a therapeutic monoclonal antibody, comprising formulating the antibody in a histidine-succinate and arginine succinate buffer, pH 4.5 to 6.5.

In certain embodiments of the formulations and methods herein, the formulation is stable. In one embodiment, the formulation is stable upon storage at about 25° C. for at least 12 months. In one embodiment, the formulation is stable upon storage at about 5° C. for at least 12 months. In one embodiment, the formulation is stable upon storage at about −20° C. for at least 12 months. In one embodiment, the formulation is stable upon storage at about 5° C. for at least 24 months. In one embodiment, the formulation is stable upon storage at about −20° C. for at least 24 months.

In certain embodiments of the formulations and methods herein, the formulation is for intravenous (IV), subcutaneous (SQ) or intramuscular (IM) administration. In one example, the formulation is for IV administration and the antibody concentration is from about 10 mg/ml to about 250 mg/ml. In another example, the formulation is for SQ administration and the antibody concentration is from about 80 mg/ml to about 250 mg/ml.

In addition, the invention concerns a method of treating a disease or disorder in a subject comprising administering the formulation to a subject in an amount effective to treat the disease or disorder.

In a still further aspect, the invention concerns a method of treating a mammal comprising administering a therapeutically effective amount of the aqueous pharmaceutical formulation disclosed herein to a mammal, wherein the mammal has a disorder requiring treatment with the antibody in the formulation. In yet another aspect, the invention provides a method of treating atherosclerosis in a subject, comprising administering the pharmaceutical formulation to the subject in an amount effective to treat the atherosclerosis. Where the antibody binds ox-LDL, examples of disorders to be treated include atherosclerosis.

These and further aspects of the invention will be apparent to those skilled in the art.

BRIEF DESCRIPTION OF THE FIGURES

FIG. 1 illustrates the nucleic acid sequence that encodes a variable heavy chain and variable light chain of an anti-oxLDL antibody.

FIG. 2 illustrates the amino acid sequence of a variable heavy chain and variable light chain of an anti-oxLDL antibody and constant region H and L.

DETAILED DESCRIPTION

Figure 3:
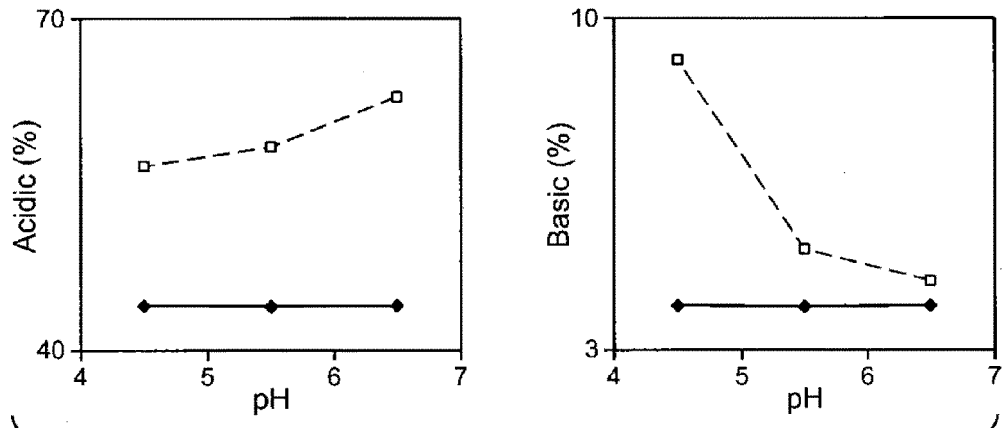
FIG. 3 illustrates charge variants of anti-oxLDL antibody by icIEF as a function of pH in the pH study of Example 1. Plot shows data at T0 (diamonds) and after incubation at 40° C. for 4 weeks (squares).

Definitions
I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

Herein, a "frozen" formulation is one at a temperature below 0° C. Generally, the frozen formulation is not freeze-dried, nor is it subjected to prior, or subsequent, lyophilization. In certain embodiments, the frozen formulation comprises frozen drug substance for storage (in stainless steel tank) or frozen drug product (in final vial configuration).

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period. In certain embodiments, the formulation is stable at about 40° C. for at least about 2-4 weeks, and/or stable at about 5° C. for at least 3 months, and/or stable at about 5° C. for at least six months, and/or stable at about 5° C. for at least 12 months and/or stable at about −20° C. for at least 3 months or at least 1 year. In certain embodiments, the formulation is stable at about 25° C. for least 6 months and/or stable at about 25° C. for 12 months, and/or stable at about 5° C. for 6 months, and/or stable at about 5° C. for 12 months, and/or stable at about −20° C. for at least 6 months, and/or stable at about −20° C. for at least 12 months, and/or stable at 5° C. or -20° C. for at least two years. In certain embodiments, the formulation is stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS—C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

Herein, "biological activity" of a monoclonal antibody refers to the ability of the antibody to bind to antigen. It can further include antibody binding to antigen and resulting in a measurable biological response which can be measured in vitro or in vivo. Such activity may be antagonistic or agonistic.

A "deamidated" monoclonal antibody herein is one in which one or more asparagine residue thereof has been derivitized, e.g. to an aspartic acid or an iso-aspartic acid.

An antibody which is "susceptible to deamidation" is one comprising one or more residue which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated at a different pH or in a different buffer.

The antibody which is formulated is preferably essentially pure and desirably essentially homogeneous (e.g., free from contaminating proteins etc). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range from about 4.5 to about 7.0, or from about 4.5 to about 6.5, or from about 5.0 to about 6.0, or has a pH of about 5.5 or has a pH of 5.5, or has a pH of about 5.6 or has a pH of 5.6. Examples of buffers that will control the pH in this range include acetate, succinate, succinate, gluconate, histidine, citrate, glycylglycine and other organic acid buffers.

A "histidine buffer" is a buffer comprising histidine ions. Examples of histidine buffers include histidine chloride, histidine acetate, histidine phosphate, histidine sulfate, histidine succinate, etc. In one embodiment, the histidine buffer identified in the examples herein was found to be histidine acetate. In the one embodiment, the histidine acetate buffer is prepared by titrating L-histidine (free base, solid) with acetic acid (liquid). In certain embodiments, the histidine buffer or histidine-acetate buffer is at pH 4.5 to 6.5. In one embodiment, the buffer has a pH 5.5. In one embodiment, the histidine buffer identified in the examples herein was found to be histidine succinate. In one embodiment, the histidine-succinate buffer is at pH 4.5 to 6.5. In one embodiment the buffer has a pH 5.5. In one embodiment, the buffer has a pH of 5.6.

A "histidine arginine buffer" is a buffer comprising histidine ions and arginine ions. Examples of histidine buffers include histidine chloride-arginine chloride, histidine acetate-arginine acetate, histidine phosphate-arginine phosphate, histidine sulfate-arginine sulfate, histidine succinate-argine succinate, etc. In one embodiment, the histidine-arginine buffer identified in the examples herein was found to be histidine acetate-arginine acetate. In the one embodiment, the histidine acetate buffer is prepared by titrating L-histidine (free base, solid) with acetic acid (liquid) and by titrating L-arginine (free base, solid) with acetic acid (liquid). In one embodiment, the histidine-arginine buffer is at pH 4.5 to 6.5. In one embodiment, the buffer has a pH of 5.5. In one embodiment, the histidine-arginine buffer identified in the examples herein was found to be histidine succinate-arginine succinate. In one embodiment, the histidine succinate-arginine succinate buffer is at pH 4.5 to 6.5. In one embodiment, the buffer has a pH of 5.5. In one embodiment, the buffer has a pH of 5.6.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl -, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20.

In a pharmacological sense, in the context of the invention, a "therapeutically effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predispose the mammal to the disorder in question.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

A "polyol" is a substance with multiple hydroxyl groups, and includes sugars (reducing and nonreducing sugars), sugar alcohols and sugar acids. A polyol may optionally be included in the formulation. In certain embodiments, polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it desired that the formulation is freeze-thaw stable, the polyol is preferably one which does not crystallize at freezing temperatures (e.g. −20° C.) such that it destabilizes the antibody in the formulation. In certain embodiments, nonreducing sugars such as sucrose and trehalose are examples of polyols, with trehalose being preferred over sucrose, because of the solution stability of trehalose.

Anti-oxLDL antibody as used herein is an antibody that binds to a protein antigen in LDL (e.g., ApoB-100). See for example, IE1-E3, LDO-D4, KTT-B8, and 2-DO3 (e.g., in WO2004/030607). ApoB-100 is the protein component of LDL which is the main carrier of cholesterol in human serum. Oxidation of LDL is an important step in its conversion to an atherogenic particle and the oxidative modifications drive the initial formation of fatty streaks, the earliest visible atherosclerotic lesion.

An example of an anti-oxLDL antibody is 2-DO3 which is a fully human monoclonal IgG1 antibody directed against oxidized LDL. The polynucleotide sequences encoding the variable heavy chain and variable light chain of antibody 2DO3 are given in FIG. 1 and have been assigned SEQ ID NO:1 and SEQ ID NO:2, respectively. The amino acid sequences of the variable heavy chain and variable light chain of the antibody 2DO3 are given in FIG. 2 and have been assigned SEQ ID NO:3 and SEQ ID NO:4, respectively. The constant region H and L have been assigned SEQ ID NO: 6 and 7, respectively, as in FIG. 2. 2-DO3 also refers with an antibody with at least the VH and VL sequences as given in FIG. 3 of WO2004/030607 (or SEQ ID No. 27 and 28 of US20040202653) and the CDR sequences of antibody as listed in table 2 of WO2007/025781.

Biological activity of an anti-oxLDL antibody would bind to ox-LDL and optionally, e.g., would inhibit plaque formation and prevent the development of atherosclerotic lesions (e.g., as described in animal models in Schiopu et al., 2004; WO 2004/030607; U.S. Pat. No. 6,716,410). Other activities include actively induce the regression of pre-existing, established atherosclerotic plaques in the aorta after a few weeks of treatment (e.g., WO2007/025781).

Atherosclerosis is a multifactorial disease developing preferentially in subjects presenting biochemical risk factors including smoking, hypertension, diabetes mellitus, hypercholesterolemia, elevated plasma low-density lipoprotein (LDL) and triglycerides, hyperfibrinogenemia and hyperglycemia. Atherosclerosis is a chronic disease that causes a thickening of the innermost layer (the intima) of large and medium-size arteries. It decreases blood flow and might cause ischemia and tissue destruction in organs supplied by the affected vessel. Atherosclerotic lesions develop over a number of decades in humans, leading to complications such as coronary and cerebral ischemic and thromboembolic diseases and myocardial and cerebral infarction.

Atherosclerosis is the major cause of cardiovascular disease including acute myocardial infarction, stroke and peripheral artery disease. The disease is initiated by accumulation of lipoproteins, primarily LDL, in the extracellular matrix of the vessel. These LDL particles aggregate and undergo oxidative modification. Oxidized LDL is toxic and causes vascular injury. Atherosclerosis represents, in many respects, a response to this injury including inflammation and fibrosis.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

The term IgG "isotype: or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g.,U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy*, Asthma & Immunol. 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147 (1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1 \times 10^{-7}$ M, preferably no more than about $1 \times 10^{-8}$ M and preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g.

residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng*, 8(10):1057-1062). Briefly, these antibodies comprise a pair of tandem Fd segments (VH—CH1-VH—CH1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol.* 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

II. Modes for Carrying Out the Invention

The invention herein relates to a formulation comprising an antibody. The antibody in the formulation is prepared using techniques available in the art for generating antibodies, exemplary methods of which are described in more detail in the following sections. Typically, the formulations are stable aqueous formulations. In certain embodiments, they are pharmaceutical formulations.

The antibody is directed against an antigen of interest. Preferably, the antigen is a biologically important polypeptide and administration of the antibody to a mammal suffering from a disorder can result in a therapeutic benefit in that mammal. However, antibodies directed against nonpolypeptide antigens are also contemplated.

Where the antigen is a polypeptide, it may be a transmembrane molecule (e.g. receptor) or ligand, e.g., such as a growth factor. Exemplary antigens include molecules such as ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tssue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); VEGFR receptors, receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β 1, TGF-β 2, TGF-β 3, TGF-β 4, or TGF-β 5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

In certain embodiments of the invention, the molecular targets for antibodies encompassed by the invention include ox-LDL. In one embodiment, the antibody herein is one which binds to human ox-LDL. In one embodiment, the antibody herein is one that bind to human ox-ApoB 100.

A. Preparation of the Formulation

After preparation of the antibody of interest (e.g., techniques for producing antibodies which can be formulated as disclosed herein will be elaborated below and are known in the art), the pharmaceutical formulation comprising it is prepared. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an F(ab')$_2$, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 0.1 mg/mL to about 250 mg/mL, or from about 10 mg/mL to about 200 mg/mL or from about 50 mg/mL to about 175 mg/mL is an exemplary antibody concentration in the formulation.

An aqueous formulation is prepared comprising the antibody in a pH-buffered solution. The buffer of this invention has a pH in the range from about 4.5 to about 6.5. In certain embodiments the pH is in the range from pH of 5.0 to 6.0, or in the range from pH 5.25 to 5.75, or in the range from pH 5.3 to 5.6. In certain embodiments of the invention, the formulation has a pH of 5.5 or about 5.5. Examples of buffers that will control the pH within this range include acetate (e.g. histidine acetate, arginine acetate, sodium acetate), succinate (such as histidine succinate, arginine succinate, sodium succinate), gluconate, citrate and other organic acid buffers and combinations thereof. The buffer concentration can be from about 1 mM to about 600 mM, depending, for example, on the buffer and the desired isotonicity of the formulation. In certain embodiments, the contain histidine in the concentration from about 5 mM to 100 mM and the arginine is in the concentration of 50 mM to 500 mM. In one embodiment, the buffer is histidine acetate (about 20 mM)-arginine acetate (about 150 mM), pH 5.5. In certain embodiments, the buffer is histidine succinate (about 20 mM)-arginine succinate (about 150 mM), pH 5.5.

A surfactant can optionally be added to the antibody formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, preferably from about 0.005% to about 0.2% and referably from about 0.01% to about 0.1%. In one embodiment, the formulation does not comprise a surfactant.

In one embodiment, the formulation contains the above-identified agents (e.g., antibody, buffer, and/or surfactant) and is essentially free of one or more preservatives, such as benzyl alcohol, phenol, m-cresol, chlorobutanol and benzethonium Cl. In one embodiment, the formulation does not comprise a preservative. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions.

While the various descriptions of chelators herein often focus on EDTA, it will be appreciated that other metal ion chelators are also encompassed within the invention. Metal ion chelators are well known by those of skill in the art and include, but are not necessarily limited to aminopolycarboxylates, EDTA (ethylenediaminetetraacetic acid), EGTA (ethylene glycol-bis(beta-aminoethyl ether)-N,N,N',N'-tetraacetic acid), NTA (nitrilotriacetic acid), EDDS (ethylene diamine disuccinate), PDTA (1,3-propylenediaminetetraacetic acid), DTPA (diethylenetriaminepentaacetic acid), ADA (beta-alaninediacetic acid), MGCA (methylglycinediacetic acid), etc. Additionally, some embodiments herein comprise phosphonates/phosphonic acid chelators. In certain embodiments, the formulation contains methionine.

The formulation herein may also contain more than one protein as necessary for the particular indication being treated, preferably those with complementary activities that do not adversely affect the other protein. For example, where the antibody is anti-oxLDL antibody, it may be combined with another agent (e.g., an inhibitor of 3-hydroxy-3-methylglutaryl-coenzyme A (HMG-CoA) reductase, e.g., statins). Examples of molecules that can be combined with anti-oxLDL antibody include but are not limited to, e.g., atorvastatin, cerivastatin, fluvastatin, lovastatin, mevastatin, provastatin, rosuvastatin, simvastatin, etc. Such proteins are suitably present in combination in amounts that are effective for the purpose intended. Typically, the statin is formulated for oral administration.

The formulations to be used for in vivo administration should be sterile. This is readily accomplished by filtration through sterile filtration membranes, prior to, or following, preparation of the formulation.

B. Administration of the Formulation

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In one embodiment, the formulation is administered to the mammal by intravenous administration. For such purposes, the formulation may be injected using a syringe or via an IV line, for example. In one embodiment, the formulation is administered to the mammal by subcutaneous administration.

The appropriate dosage ("therapeutcally effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered will be in the range of about 0.1 to about 50 mg/kg of patent body weight whether by one or more administrations, with the typical range of antibody used being about 0.3 to about 20 mg/kg, or about 0.3 to about 15 mg/kg, or about 0.3 to about 25 mg/kg or about 0.3 to about 30 mg/kg, administered daily, for example, or weekly, for example, or for example or bimonthly. However, other dosage regimens may be useful. The progress of this therapy is easily monitored by conventional techniques.

In certain embodiments of the invention, the administration of the formulation is an anti-oxLDL antibody formulation. The deposition of most cholesterol in the artery wall is derived from LDL. LDL is the main carrier of cholesterol in human serum and the oxidation of LDL is an essential step in its conversion to an atherogenic particle. Activation and regulation of the inflammatory process that characterizes all stages of atherosclerosis can be correlated to immune responses against oxidized forms of LDL. Atherosclerosis is the major cause of acute MI, stroke and peripheral artery disease. In the case of an anti-oxLDL antibody, a therapeutically effective amount of the antibody may be administered to treat atherosclerosis. For example, anti-oxLDL antibody can be used for secondary prevention of cardiovascular events in high-risk patients and/or to reduce fatal risk of atherosclerosis. These cardiovascular events, which are a direct result from atherogenic deposits in the arterial wall, include but are not limited to acute myocardial infarction (MI), stroke and peripheral artery disease. The anti-oxLDL antibody can also be used for other activities as well. For example, anti-oxLDL antibody was shown to inhibit plaque formation and prevent the development of atherosclerotic lesions (e.g., as describe in animal models in Schiopu et al., 2004; WO 2004/030607; U.S. Pat. No. 6,716,410), and actively induce the regression of pre-existing, established atherosclerotic plaques in the aorta after a few weeks of treatment (e.g., WO2007/025781).

C. Antibody Preparation (i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Voilmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA.

Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7 M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities of about $10^{-9}$ M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by antigen competition, e.g. in a procedure similar to the antigen competition method of Clackson et al., *Nature*, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma of the invention can also be modified, or example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816, 567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to certain tissues. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering,* ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as tri specific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditonal production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were finked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody of the invention is a single-domain antibody. A single-domain antibody is a single polypetide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, and Recombinant Methods

Antibodies may also be produced using recombinant methods. For recombinant production of an anti-antigent antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mix), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKDI can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 8) region where N may be any nucleotide. At the 3' end of most eukaryotic genes is an AATAAA (SEQ ID NO: 9) sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIIIE restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648, 237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crasser; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gemgross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, petunia, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

D. Selecting Biologically Active Antibodies

Antibodies produced as described above may be subjected to one or more "biological activity" assays to select an antibody with beneficial properties from a therapeutic perspective. The antibody may be screened for its ability to bind the antigen against which it was raised. For example, an anti-oxLDL antibody, as shown in the example below, the antigen binding properties of the antibody can be evaluated in an assay that detects the ability to bind to MDA-ApoB100. In certain embodiments, the antigen binding properties of the antibody can be evaluated in an assay that detects the ability to bind to ox peptide IEIGLEGKGFEPTLEALFGK (SEQ ID NO: 5). Anti-oxLDL antibodies can also be screened for those that inhibit plaque formation and prevent the development of atherosclerotic lesions in animals models (e.g., Schiopu et al., 2004; WO 2004/030607; U.S. Pat. No. 6,716,410). Other activities include actively induce the regression of pre-existing, established atherosclerotic plaques in the aorta after a few weeks of treatment (e.g., WO2007/025781).

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

To screen for antibodies which bind to a particular epitope on the antigen of interest (e.g., those which block binding of the anti-oxLDL antibody of the example to oxLDL), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

E. Articles of Manufacture

In another embodiment of the invention, an article of manufacture is provided comprising a container which holds the aqueous pharmaceutical formulation of the invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature and patent citations are incorporated herein by reference.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1

Stable Anti-oxLDL Antibody Liquid Formulations, a pH Study

These examples describe the development and stability testing of stable liquid formulations comprising anti-oxLDL antibody (having the amino acid sequence found in FIG. 2) at protein concentrations in the range from about 10 mg/mL-200 mg/mL. The antibody was developed from a recombinant antibody fragment library called n-CoDeR® that were directed against oxidized peptides derived from human ApoB-100 (e.g., WO02/080954). The stability (e.g., aggregate formulation, charge variants, etc.) of anti-oxLDL antibody was investigated in various liquid formulations consisting of histidine, arginine, acetate, sodium chloride, etc., ranging in pH from 4.5 to 6.5. The stability of anti-oxLDL antibody was monitored by several assays including UV (for concentration and turbidity), size exclusion chromatography (SEC) for size variant analysis, imaged capillary isoelectric focusing (icIEF) for charge variant analysis, and binding. After six months of stability testing, our results indicate that anti-oxLDL antibody is stable between pH 4.5 and pH 6.5 in arginine-containing buffers.

Anti-oxLDL antibody was formulated into different buffers by dialysis using Slide-a-Lyzer cassettes to achieve the final concentrations listed in Table 1. Each formulation was sterile filtered with 0.22 μm Sterifilp filter units and aseptically filled into autoclaved vials, stoppered, and sealed with aluminum flip-top seals. Samples were placed at −20° C., 2-8° C., 25° C., 30° C., 40° C. and control vials at −70° C. and stability studies were conducted up to 6-months at select temperatures.

Osmolality: The osmometer was calibrated according to the user's manual using 50 mOsm/kg and 850 mOsm/kg calibration solutions. The calibration was verified by running the Clinitrol 290 reference solution before running the formulation Protein concentration—volumetric: Concentration for all formulations was measured in duplicates after diluting samples to 0.5 mg/mL with Milli-Q water. The diluted samples were transferred to a 96-well plate (BD bioscience) and the absorbance spectra were read using a SpectraMax plate reader (Molecular Devices M2$^e$). The readings were blanked against DI water and averaged. The protein concentration was calculated according to the formula:

$$\text{Concentration (mg/mL)} = \frac{(A_{max} - A_{320}) \times \text{dilution factor (mL/mL)}}{\varepsilon \times \text{cell path length (cm)}}$$

The measured extinction coefficient (c) of anti-oxLDL antibody is 1.62 (mg/mL)$^{-1}$ cm$^{-1}$.

Viscosity: Viscosity was measured by using a Physica MCR 300 Modular Compact Rheometer, Anton Paar. A 75 μL sample was loaded in between a 25 mm cone-and-plate rheometer (1° angle; CP 25-1) at ambient temperature. Measurements were taken at a constant shear rate of 1000 sec$^{-1}$.

Activity: The biological activity of anti-oxLDL antibody was determined by measuring its ability to bind to ox-LDL in an ELISA. The ELISA-binding assay determines the ability of anti-oxLDL antibody to bind to Malondialdehyde (MDA) oxidized LDL peptide.

Size Exclusion—High Performance Liquid Chromatography (SEC): Size exclusion chromatography was used to quantitate aggregates and fragments. This assay utilizes a TSK G3000 SWXL™, 7.8×300 mm column and runs on an HP 1100™ HPLC system at 25° C. Samples were diluted to 2 mg/mL with the mobile phase and injection volume was 25 μL. The mobile phase was 0.2 M K$_2$HPO$_4$, 0.25 M KCl, at pH

TABLE 1 pH Formulation conditions

| Formulation | Buffer | [mg/mL] | pH |
|---|---|---|---|
| A | 20 mM Sodium Acetate, 150 mM Sodium Chloride, 0.02% PS20 | 170.4 | 5.5 |
| B | 20 mM Histidine Acetate, 150 mM Arginine Acetate, 0.02% PS20 | 193.6 | 4.5 |
| C | 20 mM Histidine Acetate, 150 mM Arginine Acetate, 0.02% PS20 | 189.5 | 5.5 |
| D | 20 mM Histidine Acetate, 150 mM Arginine Acetate, 0.02% PS20 | 183.3 | 6.5 |
| E | 20 mM Histidine Acetate, 150 mM Arginine Acetate 0.02% PS20 | 99.1 | 5.5 |

Methods pH: A 200 μL volume of each sample was placed in a 1.5 ml Eppendorf tubes at an ambient temperature and their pH was measured using Thermo Orion pH meter equipped with a Ross semi-micro electrode. The pH meter was calibrated using Thermo Orion buffer standards pH 4.0, 5.0 and 7.0.

Visual Inspection: The samples were analyzed visually for color, appearance, and clarity (CAC) under fluorescent light with a white and black background at ambient temperature.

Turbidity: The turbidity of the formulation samples was measured by the absorbance of 360 nm and 450 nm using a SpectraMax M2e plate reader. 100 μL of undiluted samples were loaded on a 96-well micro plate and turbidity was measured against a water blank. In order to compare formulations of different protein concentrations, the absorbance at 360 nm and 450 nm were divided by the protein concentration to normalize for any effects caused solely by the amount of protein present.

6.2 and the protein was eluted at a steady flow rate of 0.5 ml/min for 30 minutes. The eluent absorbance was monitored at 280 nm. Integration was done using HP CHEMSTATIONM™ software.

Image capillary isoelectric focusing (icIEF): The stability samples stored at 40° C. and a reference sample were assayed using icIEF to quantify charge (acidic and basic) variants of anti-oxLDL antibody stability samples. This technique uses a fluorocarbon coated capillary in a FAST IEF analyzer with a Prince auto sampler.

Ion-Exchange Chromatography (IEX): Cation exchange chromatography was employed to measure changes in charge variants. This assay utilizes a DIONEX PROPAC WCX-10™ column on an HP 1100™ HPLC system. Samples were diluted to 2 mg/mL with the mobile phase A containing 50 mM HEPES at pH 7.5. 25 μl of diluted samples were then loaded on the column that was kept at ambient temperature (40° C.). The peaks were eluted using mobile B containing 50 mM HEPES, 100 mM sodium sulfate, pH 7.5. The eluent was monitored at 280 nm. The data were analyzed using HP CHEMSTATION® software.

Result and Discussion

In this formulation pH study, the effect of protein concentration, ionic strength and solution pH on the stability of anti-oxLDL antibody was investigated. SEC, IEC, icIEF and turbidity assays were used to monitor stability of anti-oxLDL antibody at real-time and accelerate storage conditions. Protein concentration, osmolality, viscosity, binding and CE-SDS assays were performed at selected time points. This study investigated the stability (e.g., aggregate formation, charge variants, etc.) of different concentrations of anti-oxLDL antibody in an arginine-based formulation over a pH range of pH 4.5 to pH 6.5. L-arginine was used to formulate high ionic strength buffers. The osmolality, pH, protein concentration, and viscosity were measured and shown below (Table 2).

TABLE 2 physical properties of formulations studied

| Formulation | [Protein] (mg/ml) | Osmolality (mOsm/kg) | Viscosity (cP) | pH |
|---|---|---|---|---|
| A | 170.4 | 326 | 7.8 | 5.5 |
| B | 193.6 | 495 | 6.9 | 4.5 |
| C | 189.5 | 389 | 10.7 | 5.5 |
| D | 183.3 | 344 | 10.9 | 6.5 |
| E | 99.1 | 358 | 2.5 | 5.5 |

All formulations were exposed to three cycles of freezing at either −20° C. or −70° C. and then subsequently cooled at ambient temperature. SEC confirmed that freezing did not significantly change the physical property of anti-oxLDL antibody at −70° C. and −20° C. for the formulations listed in Table 1 (See Table 2).

Binding Activity of all Formulations at 40° C.: The binding activity of samples was measured an ELISA-binding assay to oxLDL. The assay showed that all formulations tested after four weeks of incubation at 40° C. had dropped to ~20% of the control sample (@ T0) (Table 3).

TABLE 3

| Assay at 40° C. for 4-week formulations | |
|---|---|
| Sample, storage temp | 4 weeks |
| A, 40 C. | 76.6 ± 5.4% |
| B, 40 C. | 71.1 ± 6.1% |
| C, 40 C. | 77.6 ± 1.7% |
| D, 40 C. | 86.1 ± 3.9% |
| E, 40 C. | 79.0 ± 2.8% |

Effect of pH: Size, charge variant, and turbidity assays were used to monitor the stability of anti-oxLDL antibody at various temperatures over time. SEC was used to determine amount of aggregate, monomer and fragment generated while IEC was used to determine acidic, main and basic variants generated during the stability study (FIG. 3). The IEC method used was not a stability indicating assay for all anti-oxLDL antibody formulations tested, so then we used icIEF which separates charges by a different mechanism. At solution pH 4.5, anti-oxLDL antibody formed more basic variants while more acidic variants were formed at pH 6.5 (FIG. 3).

Figure 4:
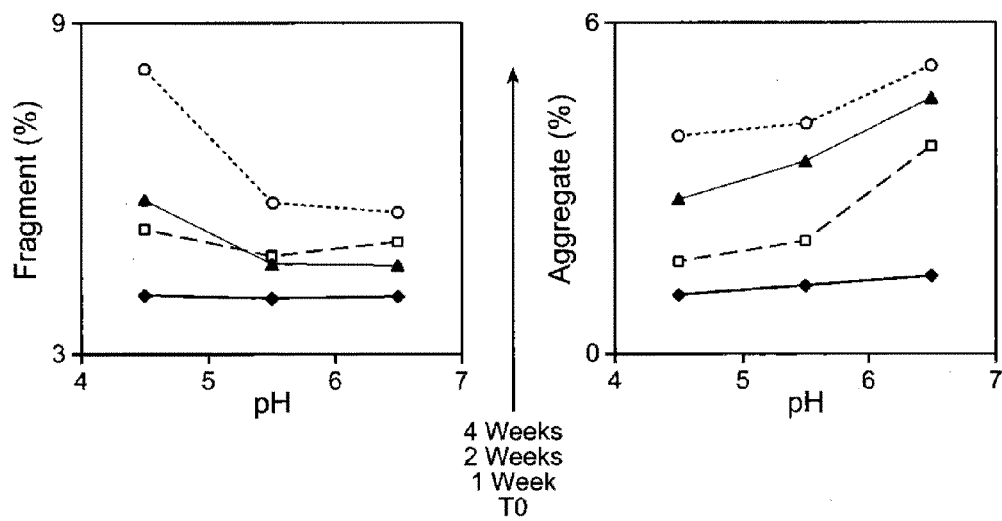
FIG. 4 illustrates size variants of anti-oxLDL antibody as a function of pH at 40° C. Plot shows data at T0 (diamonds), one week (squares), two weeks (triangles), and four weeks (circles) (pH study).

These results were complemented with a SEC study which showed that at 40° C. anti-oxLDL antibody readily aggregates at pH 6.5 and fragments at pH 4.5 (FIG. 4). SEC and IcIEF data both suggested that at 40° C., anti-oxLDL antibody is more stable at pH 5.5 compared to pH 4.5 and pH 6.5 samples tested.

Turbidity of samples were measured at 360 nm and 450 nm wavelengths and normalized to protein concentration. The normalized sample turbidity observed increased slightly with time at 30° C. and 40° C.; however no precipitation was observed.

Effect of Excipients and Ionic Strength: The effect of different excipients on the stability of anti-oxLDL antibody was investigated. A list of excipients explored includes sodium chloride, sodium acetate, histidine acetate, and arginine acetate. Our results showed that formulations containing sodium chloride aggregated faster than all other formulations.

Effect of Anti-oxLDL antibody Concentration: Protein concentration did not have a strong effect on the stability of anti-oxLDL antibody as suggested by size and charge variant assays. Aggregation appeared slightly dependent on concentration between 99 mg/ml and 189 mg/ml with the higher concentration having slightly more aggregation. SEC was used to determine amount of aggregate, monomer and fragment generated while icIEF was used to determine acidic, main and basic variants generated during the stability study.

The stability of anti-oxLDL antibody was evaluated in various buffer conditions. The data obtained from the formulation screening study showed that anti-oxLDL antibody is more stable in histidine acetate and arginine acetate buffers between pH 4.5 and pH 6.5.

Example 2

Stable Anti-oxLDL Antibody Liquid Formulations, an Excipient Study

The stability of anti-oxLDL antibody was evaluated in various liquid (histidine acetate, histidine sulfate, histidine succinate, histidine citrate, and PBS) formulations (Table A). One milliliter of each formulation in a 3 cc glass vials was stored at −70, −20, 5, 25, 30 and 40° C. for up to a period of 6 months and the stability was assessed at 1, 2, 4, 6, 8, 12 and 24 weeks. The stability of anti-oxLDL antibody was monitored by several assays including UV (for concentration and turbidity), size exclusion chromatography (SEC) for size variant analysis, imaged capillary isoelectric focusing (icIEF) for charge variant analysis, CE-SDS for size distribution and binding assay for activity. After six months of stability testing, our results indicate anti-oxLDL antibody is stable in 20 mM histidine acetate, 150 mM arginine acetate, 0.02% polysorbate 20, pH 5.5.

Sample preparation: Anti-oxLDL antibody was formulated into different buffers by dialysis using Slide-a-Lyzer cassettes followed by protein concentration using Amicon Ultra-15 centrifugation device to reach the target concentration. Polysorbate 20, polysorbate 80, methionine, and EDTA were added to achieve the final concentrations listed in Table A. Each formulation was sterile filtered with 0.22 μm Sterifilp filter units and aseptically filled into autoclaved vials, stoppered, and sealed with aluminum flip-top seals. All samples in the below formulations were kept as liquid. Samples were placed at −20° C., 2-8° C., 25° C., 30° C., 40° C. and control vials at −70° C. and stability studies were conducted up to 6-months at select temperatures.

TABLE A

Formulation conditions

| Formulation | Buffer | pH | protein conc. (mg/mL) |
|---|---|---|---|
| 1 | 20 mM Histidine Acetate, 150 mM Arginine Acetate, 0.02% PS20 | 5.6 | 25.0 |
| 2 | 20 mM Histidine Acetate, 150 mM Arginine Acetate, 0.02% PS20 | 5.6 | 50.0 |
| 3 | 20 mM Histidine Acetate, 150 mM Arginine Acetate, 0.02% PS20 | 5.6 | 158.0 |
| 4 | 20 mM Histidine Sulfate, 150 mM Arginine Sulfate 0.02% PS20 | 5.8 | 156.0 |
| 5 | 20 mM Histidine Succinate, 150 mM Arginine Succinate, 0.02% PS20 | 5.6 | 164.0 |
| 6 | 20 mM Histidine Citrate, 150 mM Arginine Citrate, 0.02% PS20 | 5.7 | 182.0 |
| 7 | 20 mM Histidine Acetate, 150 mM Arginine Acetate, 0.05% PS80 | 5.6 | 156.0 |
| 8 | 20 mM Histidine Acetate, 150 mM Arginine Acetate, 0.2% PS20 | 5.6 | 154.0 |
| 9 | 20 mM Histidine Acetate, 150 mM Arginine Acetate, 5 mg/mL Methionine 0.02% PS20 | 5.6 | 136.0 |
| 10 | PBS (137 mM NaCl, 10 mM Phosphate, 2.7 mM KCl) 0.02% PS20 | 7.4 | 152.0 |
| 11 | 20 mM Histidine Acetate, 150 mM Arginine Acetate, 0.02% PS20 1 mM EDTA | 5.6 | 154.0 |

Methods pH: A 200 µL of each sample was placed in a 1.5 ml Eppendorf tubes at an ambient temperature and their pH was measured using Thermo Orion pH meter equipped with a Ross semi-micro electrode. The pH meter was calibrated using Thermo Orion buffer standards pH 4.0, 5.0 and 7.0.

Visual Inspection: The samples were analyzed visually for color, appearance, and clarity (CAC) under fluorescent light with a white and black background at ambient temperature.

Turbidity: The turbidity of the formulation samples was measured by the absorbance of 360 nm and 450 nm using a SpectraMax M2$^e$ plate reader. A 100 µL of undiluted samples and water (for blanking) were loaded on a 96-well micro plate and turbidity was measured. In order to compare formulations of different protein concentrations, the absorbance at 360 nm and 450 nm were divided by the protein concentration to normalize for any effects caused solely by the amount of protein present.

Osmolality: The osmometer was calibrated according to the user's manual using 50 mOsm/kg and 850 mOsm/kg calibration solutions. The calibration was verified by running the Clinitrol 290 reference solution before running the formulation samples.

Protein concentration—volumetric: Concentration for all formulations was measured in duplicates after diluting samples to 0.5 mg/mL with Milli-Q water. The diluted samples were transferred to a 96-well plate (BD bioscience, cat# 353261) and the concentration was read using a SpectraMax plate reader (Molecular Devices M2$^e$). The readings were blanked against DI water and averaged. The protein concentration was calculated according to the formula:

$$\text{Concentration (mg/mL)} = \frac{(A_{max} - A_{320}) \times \text{dilution factor (mL/mL)}}{\varepsilon \times \text{cell path length (cm)}}$$

The measured extinction coefficient ($\varepsilon$) of anti-oxLDL antibody is 1.62 $(\text{mg/mL})^{-1} \text{cm}^{-1}$.

Viscosity: Viscosity was measured by using a Physica MCR 300 Modular Compact Rheometer, Anton Paar. A 75 µL sample was loaded in between a 25 mm cone-and-plate rheometer (1° angle; CP 25-1) at ambient temperature. Measurements were taken at a constant shear rate of 1000 $\text{sec}^{-1}$.

Binding Assay: The 4-weeks stability samples stored at 40° C. were diluted to 0.5 mg/mL with Milli-Q water and were tested for oxLDL binding in an ELISA. A sample that has not gone though the thermal degradation process was used as an assay control.

CE-SDS UV (non-reduced): The 4-week stability samples stored at 40° C. and a reference sample were assayed using CE-SDS UV non-reducing method to assess the size distribution of anti-oxLDL antibody stability samples.

Size Exclusion—High Performance Liquid Chromatography (SEC): Size exclusion chromatography was used to quantitate aggregates and fragments. This assay utilizes a TSK G3000 SWXL™, 7.8×300 mm column and runs on an HP 1100™ HPLC system. Samples were diluted to 2 mg/mL with the mobile phase and injection volume was 25 µL. The mobile phase was 0.2 M $K_2HPO_4$, 0.25 M KCl, at pH 6.2 and the protein was eluted at a steady flow rate of 0.5 mL/min for 30 minutes. The eluent absorbance was monitored at 280 nm. Integration was done using HP CHEMSTATIONM™ software.

Image capillary isoelectric focusing (icIEF): The stability samples stored at 40° C. and a reference sample were assayed using icIEF to quantify charge (acidic and basic) variants of anti-oxLDL antibody stability samples. This technique uses a fluorocarbon coated capillary in a FAST IEF analyzer with a Prince auto sampler.

Result and Discussion

In this formulation excipient study, the effects of different buffer counter ions, surfactants and anti-oxidizing agents on the stability of anti-oxLDL antibody were investigated. SEC, icIEF and turbidity assays were used to monitor the stability of anti-oxLDL antibody throughout the study. Protein concentration, osmolality, viscosity, potency and CE-SDS assays were performed on select stability samples and time points. The buffer concentration of 20 mM and a around pH 5.5 was selected based on results from a previous pH study. The pH of all liquid formulations was measured after buffer exchange (Table A). The osmolality, pH, protein concentration, and viscosity were measured and shown below (Table B). The results from the visual inspection assay showed that all samples look clear with pale yellow in color.

TABLE B physical properties of formulations studied

| Formulation | protein conc. (mg/mL) | Osmolality (mOsm/kg) | Viscosity | pH |
|---|---|---|---|---|
| 1 | 25.00 | 348 | 1.22 | 5.6 |
| 2 | 50.00 | 352 | 1.58 | 5.6 |
| 3 | 158.00 | 376 | 5.39 | 5.6 |
| 4 | 156.00 | 256 | 5.64 | 5.8 |
| 5 | 164.00 | 244 | 5.58 | 5.6 |
| 6 | 182.00 | 194 | 8.79 | 5.7 |

TABLE B-continued physical properties of formulations studied

| Formulation | protein conc. (mg/mL) | Osmolality (mOsm/kg) | Viscosity | pH |
|---|---|---|---|---|
| 7 | 156.00 | 384 | 5.21 | 5.6 |
| 8 | 154.00 | 377 | 4.87 | 5.6 |
| 9 | 136.00 | 410 | 4.23 | 5.6 |
| 10 | 152.00 | 310 | 6.46 | 7.4 |
| 11 | 154.00 | 397 | 4.89 | 5.6 |

A set of formulations that were stored in −20° C. and −70° C. were subjected to three freeze-thaw cycles over one week period. Samples were frozen at −20° C. and −70° C. respectively then thawed at ambient temperature. The physical properties of the samples that underwent freeze-thaw cycles were evaluated by size exclusion chromatography. The SEC assay confirmed that freeze-thaw did not affect the percentage of aggregates or fragments of the samples tested.

The turbidity of samples measured at 360 nm and 450 nm wavelengths showed that there is no substantial change in turbidity for most formulations stored at 5° C. over time. The turbidity for the formulation samples increased slightly with temperature (25° C., 30° C. and 40° C.) and time.

Figure 5:
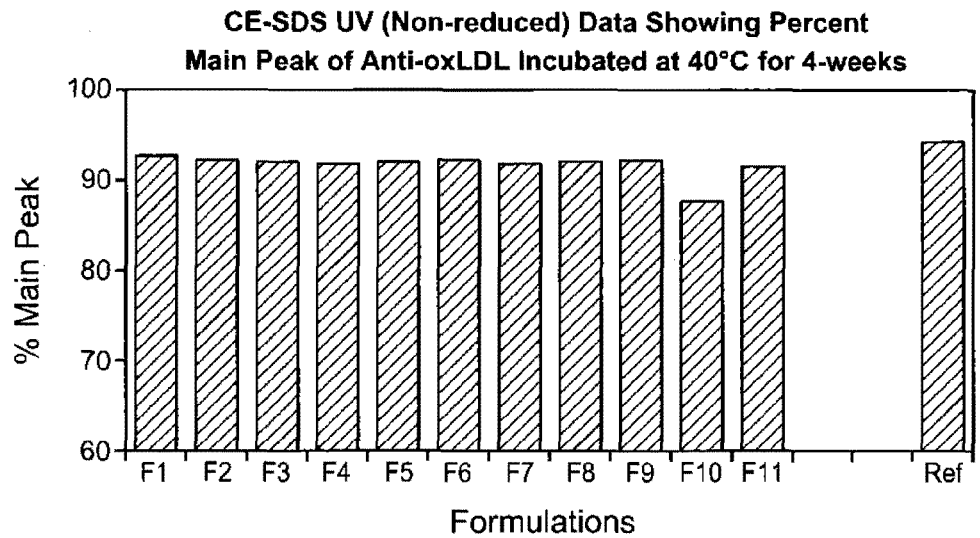
FIG. 5 illustrates CE-SDS UV (non-reduced) data showing percent main peak of anti-oxLDL antibody incubated at 40° C. for 4-weeks (excipient study).

CE-SDS UV is a quantitative assay used for the estimation of apparent molecular weight of protein covalent aggregates, fragments and monomers, such as free light or heavy chain in antibody preparations. The CE-SDS assay was run in a non-reduced condition using stability samples stored at 40° C. for 4-weeks. The results showed that the percentage of the main peak for all the samples tested were within the acceptable assay ranges (FIG. 5).

Figure 6:
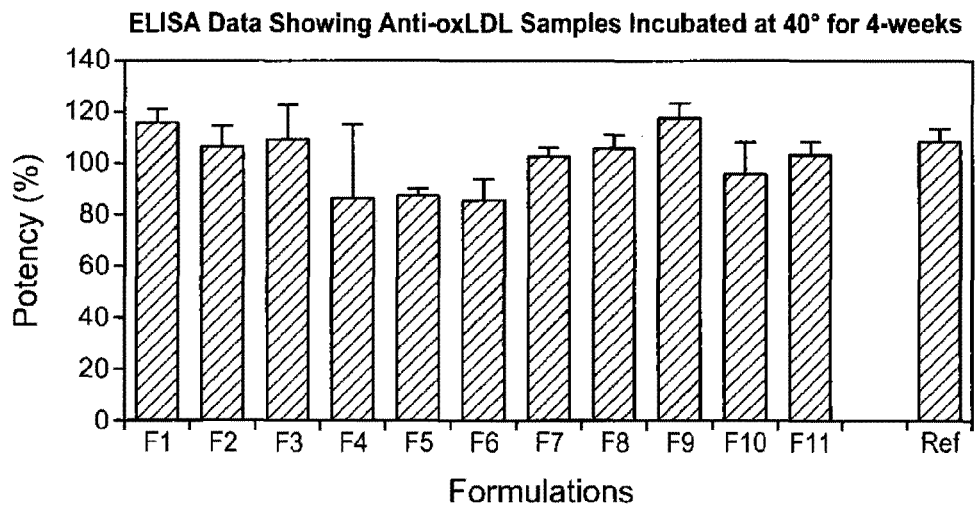
FIG. 6 illustrates ELISA binding data showing anti-oxLDL antibody samples incubated at 40° C. for 4-weeks.

The binding activity of samples was measured using ELISA-binding assay. The ELISA-binding assay determines the ability of anti-oxLDL antibody to bind to Malondialdehyde (MDA) oxidized LDL peptide. The assay results showed that all formulations tested after 4-weeks of incubation at 40° C. were within the acceptable assay range of +/−25% (FIG. 6).

Figure 7A:
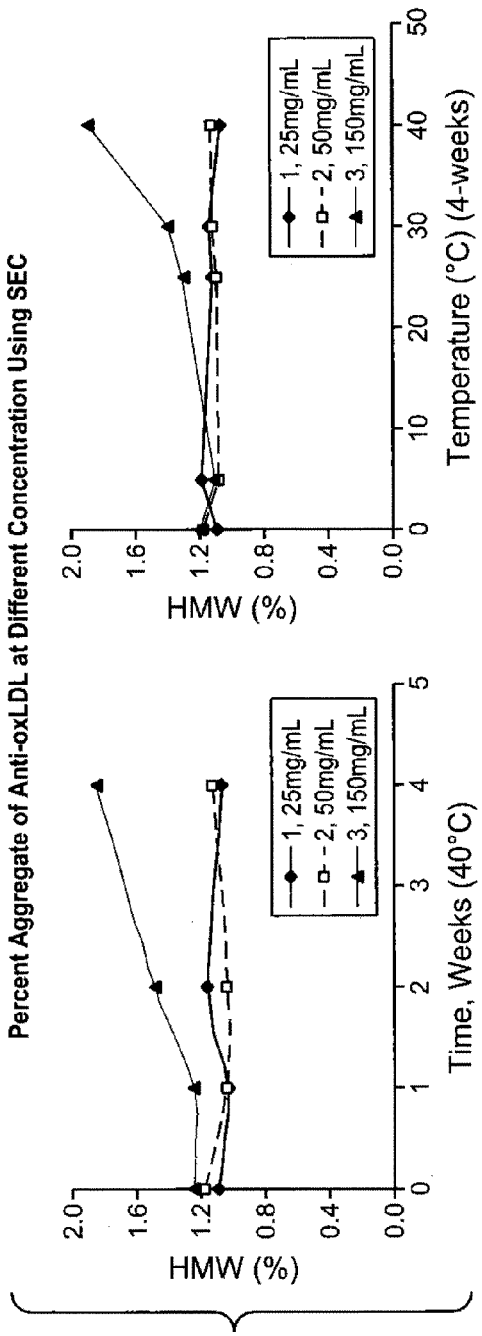
FIGS. 7 A and B illustrate (A) percent aggregate of anti-oxLDL antibody at different concentrations using SEC, and (B) percent acidic peak of anti-oxLDL antibody at different concentrations using icIEF.
Figure 7B:
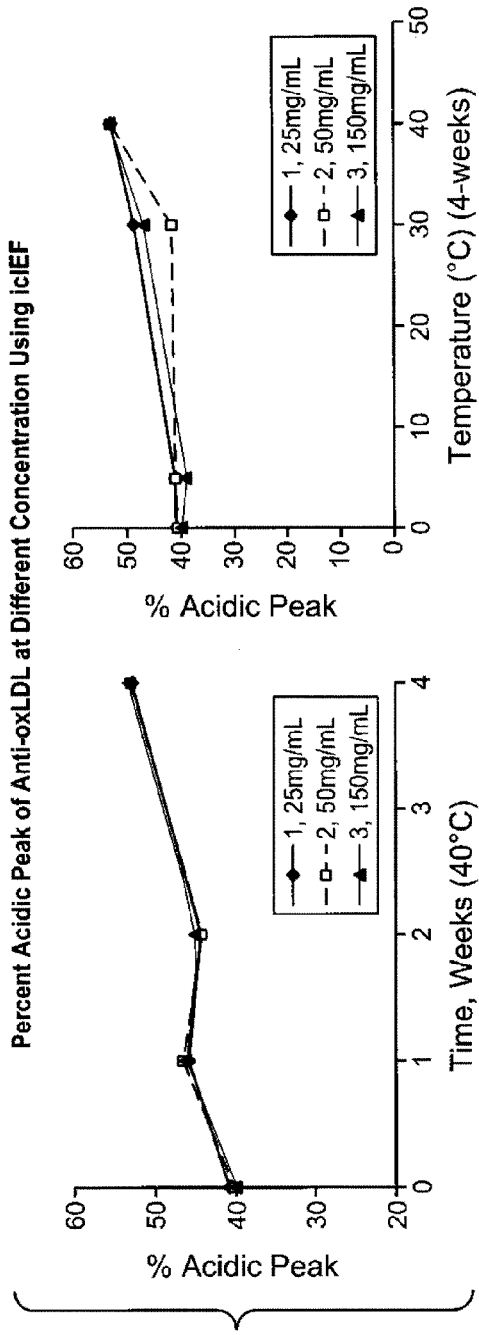

Effect of anti-oxLDL antibody Concentration: Three different concentrations (25 mg/mL (1), 50 mg/mL (2) and 150 mg/mL (3)) formulated in 20 mM histidine acetate, 150 mM arginine acetate, 0.02% PS20 pH 5.5 and stored at 40° C. for up to 4 weeks were assayed to investigate the effect of concentration on the stability of anti-oxLDL antibody. The results showed that there is no significant time and temperature dependent aggregate formation for the 25 mg/mL and the 50 mg/mL formulations where as there is an increase in aggregate formation for the 150 mg/mL formulation samples. The icIEF assay result showed that there is time and temperature dependent increase of the acidic variant for all three concentrations studied (FIGS. 7A and B).

Effect of excipients: The effect of different excipients on the stability of anti-oxLDL antibody was investigated. A list of excipients explored includes phosphate-buffered-saline (PBS), histidine-hydrochloride, and counter ions to arginine (acetate, sulfate, succinate, and citrate). The results showed that there were no significant changes in aggregates, fragments, acidic, and basic variants for arginine containing formulations irrespective of its counter ion. In the presence of PBS, there was a significant increase in aggregation, fragmentation, and acidic variants over time in all temperatures studied.

Figure 8:
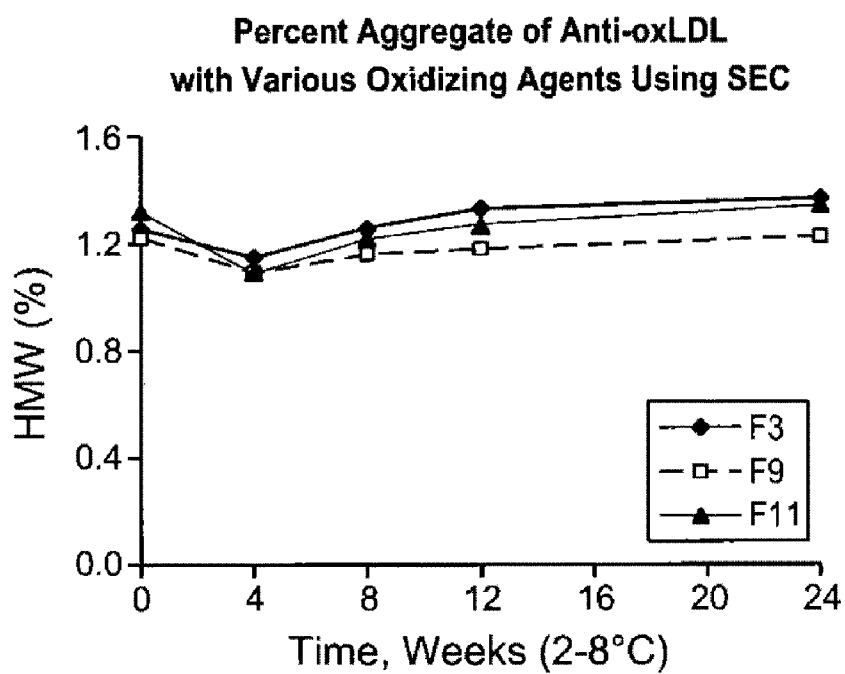
FIG. 8 illustrates percent aggregate of anti-oxLDL antibody with various oxidizing agents using SEC.

Surfactant: Surfactants provide protection against agitation-induced aggregation as well as against adsorption-induced loss of protein. The effect of non-ionic surfactants on the stability of anti-oxLDL antibody was mitigated by using polysorbate 20 (at 0.02% and 0.2%) and polysorbate 80 (at 0.05%). The results showed that 0.02% polysorbate 20 is sufficient to keep the protein stable. Increasing polysorbate concentration to 0.2% or using a higher molecular weight surfactant, polysorbate 80, did not provide any stability advantages to anti-oxLDL antibody. (FIG. 8)

Anti-oxidizing agents: Methionine (5 mg/mL) and EDTA (1 mM) were used as anti-oxidants in formulations 9 and 11 respectively. EDTA chelates metal ions and hence prevents metal-induced oxidation, while methionine has the ability to scavenge oxidizing species. The results from the SEC assay showed that EDTA and methionine only slightly improved the stability of anti-oxLDL antibody at 2-8° C. (FIG. 8).

The stability of anti-oxLDL antibody was evaluated in various buffer conditions. The data obtained from the formulation screening study showed that anti-oxLDL antibody is stable at 150 mg/mL protein concentration in 20 mM histidine acetate, 150 mM arginine acetate, 0.02% polysorbate 20 at around pH 5.5.

I claim:

1. A formulation comprising a therapeutically effective amount of an anti-oxLDL antibody in a histidine-arginine buffer, pH 4.5 to 6.5, wherein the buffer is a histidine acetate-arginine acetate buffer or a histidine succinate-arginine succinate buffer, and wherein the anti-oxLDL antibody comprises a heavy chain variable region comprising the amino acid sequence of SEQ ID NO:3, and a light chain variable region comprising the amino acid sequence of SEQ ID NO:4.

2. The formulation of claim 1, wherein the buffer is a histidine acetate-arginine acetate buffer, pH 5.0 to 6.0 or wherein the buffer is a histidine succinate-arginine succinate buffer, pH is 5.0 to 6.0.

3. The formulation of claims 2, wherein histidine acetate or histidine succinate concentration in the buffer is from 5 mM to 100 mM.

4. The formulation of claims 2, wherein the histidine acetate or histidine succinate concentration is 20 mM.

5. The formulation of claims 2, wherein arginine acetate or arginine succinate concentration in the buffer is from 50 mM to 500 mM.

6. The formulation of claims 2, wherein the arginine acetate or arginine succinate concentration is 150 mM.

7. The formulation of claim 1, further comprising a surfactant.

8. The formulation of claim 7, wherein the surfactant is polysorbate.

9. The formulation of claim 8, wherein the polysorbate is polysorbate 20.

10. The formulation of claim 9, wherein the surfactant concentration is from 0.0001% to 1.0%.

11. The formulation of claim 10, wherein the surfactant concentration is from 0.01% to 0.1%.

12. The formulation of claim 11, wherein the surfactant concentration is 0.02%.

13. The formulation of claim 1, wherein the antibody concentration is from 10 mg/ml to 250 mg/ml.

14. The formulation of claim 1, wherein the antibody concentration is from 100 mg/ml to 250 mg/ml.

15. The formulation of claim 1, wherein the antibody concentration is from 150 mg/ml to 200 mg/ml.

16. The formulation of claim 1, wherein the antibody concentration is from 25 mg/ml to 200 mg/ml.

17. The formulation of claim 1, wherein the antibody is not subject to prior lyophilization.

18. The formulation of claim 1 further comprising methionine.

19. The formulation of claim 18, wherein the methionine concentration is 5 mg/ml.

20. The formulation of claim 1, further comprising EDTA.

21. The formulation of claim 20, wherein the EDTA concentration is 1 mM EDTA.

22. The formulation of claim 7, wherein the buffer is 20 mM histidine acetate and 150 mM arginine acetate pH 5.5, the surfactant is polysorbate in an amount of 0.01-0.1% v/v, wherein the formulation is stable at a temperature of 2-8° C. for at least 12 months or wherein the buffer is 20 mM histidine succinate and 150 mM arginine succinate pH 5.5, the surfactant is polysorbate in an amount of 0.01-0.1% v/v, wherein the formulation is stable at a temperature of 2-8° C. for at least 12 months.

23. The formulation of claim 1, wherein the formulation is a pharmaceutical formulation.

24. The formulation of claim 1, wherein the formulation is stable upon storage at 25° C. for at least 12 months or wherein the formulation is stable upon storage at 5° C. for at least 12 months or wherein the formulation is stable upon storage at −20° C. for at least 12 months.

25. An article of manufacture comprising a container holding an aqueous pharmaceutical formulation comprising a therapeutically effective amount of an anti-oxLDL antibody, a histidine acetate-arginine acetate buffer from pH 5.0 to 6.0, and a surfactant, or comprising a container holding an aqueous pharmaceutical formulation comprising a therapeutically effective amount of an anti-oxLDL antibody, a histidine succinate-arginine succinate buffer from pH 5.0 to 6.0, and a surfactant; wherein the anti-oxLDL antibody comprises a heavy chain variable region comprising the amino acid sequence of SEQ ID NO:3, and a light chain variable region comprising the amino acid sequence of SEQ ID NO:4.

26. A method for stabilizing an anti-oxLDL antibody in an aqueous pharmaceutical formulation comprising combining a therapeutically effective amount of the antibody, a histidine acetate-arginine acetate buffer from pH 5.0 to 6.0, and a surfactant, or comprising combining a therapeutically effective amount of the antibody, a histidine succinate-arginine succinate buffer from pH 5.0 to 6.0, and a surfactant; wherein the anti-oxLDL antibody comprises a heavy chain variable region comprising the amino acid sequence of SEQ ID NO:3, and a light chain variable region comprising the amino acid sequence of SEQ ID NO:4.

27. A pharmaceutical formulation comprising: (a) a full length anti-oxLDL IgG1 antibody susceptible to deamidation or aggregation in an amount from 10 mg/mL to 250 mg/mL; wherein the anti-oxLDL antibody comprises a heavy chain variable region comprising the amino acid sequence of SEQ ID NO:3, and a light chain variable region comprising the amino acid sequence of SEQ ID NO:4; (b) histidine acetate-arginine acetate buffer, pH 5.0 to 6.0; and (c) polysorbate 20 in an amount from 0.01% to 0.1%.

28. A pharmaceutical formulation comprising: (a) a full length anti-oxLDL IgG1 antibody susceptible to deamidation or aggregation in an amount from 10 mg/mL to 250 mg/mL; wherein the anti-oxLDL antibody comprises a heavy chain variable region comprising the amino acid sequence of SEQ ID NO:3, and a light chain variable region comprising the amino acid sequence of SEQ ID NO:4; (b) histidine succinate-arginine succinate buffer, pH 5.0 to 6.0; and (c) polysorbate 20 in an amount from 0.01% to 0.1%.

29. The formulation of claim 1, wherein the anti-oxLDL antibody is a human IgG1 antibody.

30. The formulation of claim 1, wherein the anti-oxLDL antibody is a chimeric anti-oxLDL antibody.

31. The method of claim 1, wherein the anti-oxLDL antibody is a human anti-oxLDL antibody.

32. The formulation of claim 1, wherein the anti-oxLDL antibody is an antibody fragment selected from the group consisting of a Fab, Fab', F(ab')$_2$ and Fv fragment.

33. The formulation of claim 7, wherein the buffer is 20 mM histidine acetate and 150 mM arginine acetate pH 5.5, and the surfactant is polysorbate 20 in an amount of 0.01-0.1% v/v.

34. The formulation of claim 7, wherein the buffer is 20 mM histidine succinate and 150 mM arginine succinate pH 5.5, the surfactant is polysorbate 20 in an amount of 0.01-0.1% v/v.

35. The article of manufacture of claim 25, wherein the anti-oxLDL antibody is a human IgG1 antibody.

36. The article of manufacture of claim 25, wherein the anti-oxLDL antibody is a human anti-oxLDL antibody.

37. The article of manufacture of claim 25, wherein the anti-oxLDL antibody is an antibody fragment selected from the group consisting of a Fab, Fab', F(ab')$_2$ and Fv fragment.

38. The method of claim 26, wherein the anti-oxLDL antibody is a human IgG1 antibody.

39. The method of claim 26, wherein the anti-oxLDL antibody is a human anti-oxLDL antibody.

40. The method of claim 26, wherein the anti-oxLDL antibody is an antibody fragment selected from the group consisting of a Fab, Fab', F(ab')$_2$ and Fv fragment.

41. The pharmaceutical formulation of claim 27, wherein the anti-oxLDL antibody is a human IgG1 antibody.

42. The pharmaceutical formulation of claim 27, wherein the anti-oxLDL antibody is a human anti-oxLDL antibody.

43. The pharmaceutical formulation of claim 28, wherein the anti-oxLDL antibody is a human IgG1 antibody.

44. The pharmaceutical formulation of claim 28, wherein the anti-oxLDL antibody is a human anti-oxLDL antibody.

* * * * *